(12) United States Patent
Mayeaux

(10) Patent No.: US 7,886,624 B1
(45) Date of Patent: *Feb. 15, 2011

(54) PORTABLE INSERTABLE PROBE ASSEMBLY INCLUDING HAZARDOUS OPERATIONS CAPABILITY

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 555 days.

This patent is subject to a terminal disclaimer.

(21) Appl. No.: 11/836,431

(22) Filed: Aug. 9, 2007

Related U.S. Application Data

(63) Continuation-in-part of application No. 11/151,186, filed on Jun. 13, 2005, now Pat. No. 7,472,615.

(60) Provisional application No. 60/646,332, filed on Jan. 24, 2005.

(51) Int. Cl.
*G01M 19/00* (2006.01)

(52) U.S. Cl. .................................................. 73/866.5

(58) Field of Classification Search ................ 73/866.5
See application file for complete search history.

(56) References Cited

U.S. PATENT DOCUMENTS

| | | | | |
|---|---|---|---|---|
| 3,691,846 A | * | 9/1972 | Ingold | 73/866.5 |
| 3,831,953 A | | 8/1974 | Leibfritz et al. | 277/637 |
| 3,835,710 A | | 9/1974 | Pogorski | 73/864.74 |
| 4,014,216 A | | 3/1977 | Thornton et al. | 73/863.23 |
| 4,070,239 A | * | 1/1978 | Bevilacqua | 376/245 |
| 4,112,768 A | | 9/1978 | Holland et al. | 73/863.24 |
| 4,157,040 A | | 6/1979 | Barton et al. | 73/863.23 |
| 4,800,763 A | | 1/1989 | Hakkers et al. | 73/863 |
| 4,821,585 A | | 4/1989 | Kempe | 73/863.23 |
| 4,865,811 A | | 9/1989 | Newton et al. | 422/81 |
| 4,928,541 A | | 5/1990 | Toon et al. | 73/868.63 |
| 5,205,988 A | | 4/1993 | Tanaka et al. | 422/91 |
| 5,442,969 A | | 8/1995 | Troutner et al. | 73/863.85 X |
| 5,637,792 A | | 6/1997 | Kimura et al. | 73/116 |
| 5,814,741 A | | 9/1998 | Wang et al. | 73/863.12 |
| 5,844,123 A | | 12/1998 | Marsh et al. | 73/863.12 |
| 7,617,745 B1 | * | 11/2009 | Mayeaux | 73/866.5 |

FOREIGN PATENT DOCUMENTS

| | | | | |
|---|---|---|---|---|
| JP | 6-288880 | 10/1994 | | 73/863 |
| WO | 95/02176 | 1/1995 | | |

* cited by examiner

*Primary Examiner*—Thomas P Noland
(74) *Attorney, Agent, or Firm*—Joseph T Regard Ltd plc

(57) ABSTRACT

An assembly for insertion and retraction of probe or probe-like device which does not require a seal or packing gland, instead utilizing pressure equalization between pressurized process fluids and the housing containing a probe, so as to negate the use of a dynamic seal. The preferred embodiment of the present invention contemplates an inserting/retraction mechanism for raising and lowering the probe into and from the pressurized fluid, respectively. A housing having a valve is configured to allow fluid communication between the pressurized fluid source, and the interior of the housing assembly. A conduit engages the housing assembly, and is formed to slidingly receive the outer diameter of the probe therethrough, such that a sliding seal maintains a fluid seal between the outer wall of the probe and the inner wall of the conduit, as the probe is telescoped therethrough during insertion and retraction of the probe into/from the pressurized process.

20 Claims, 23 Drawing Sheets

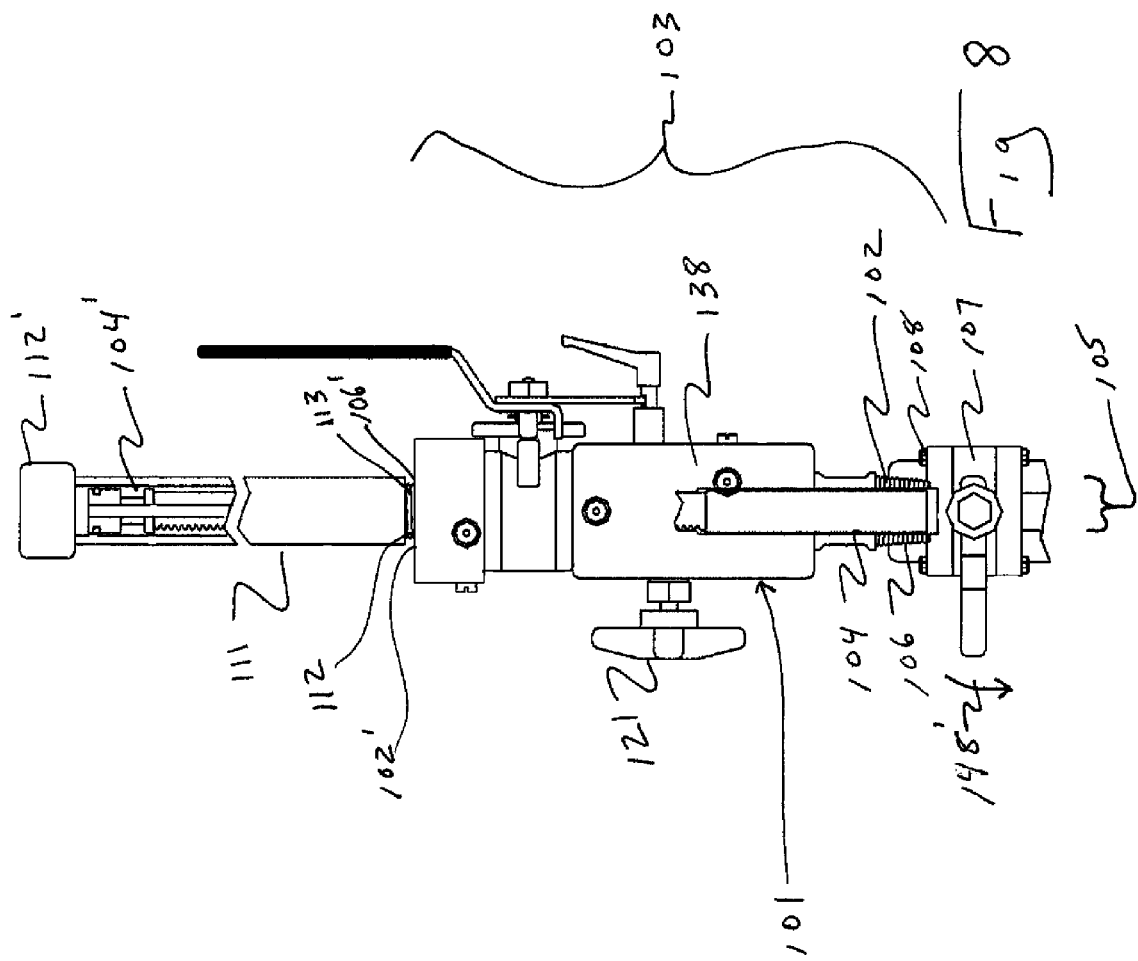

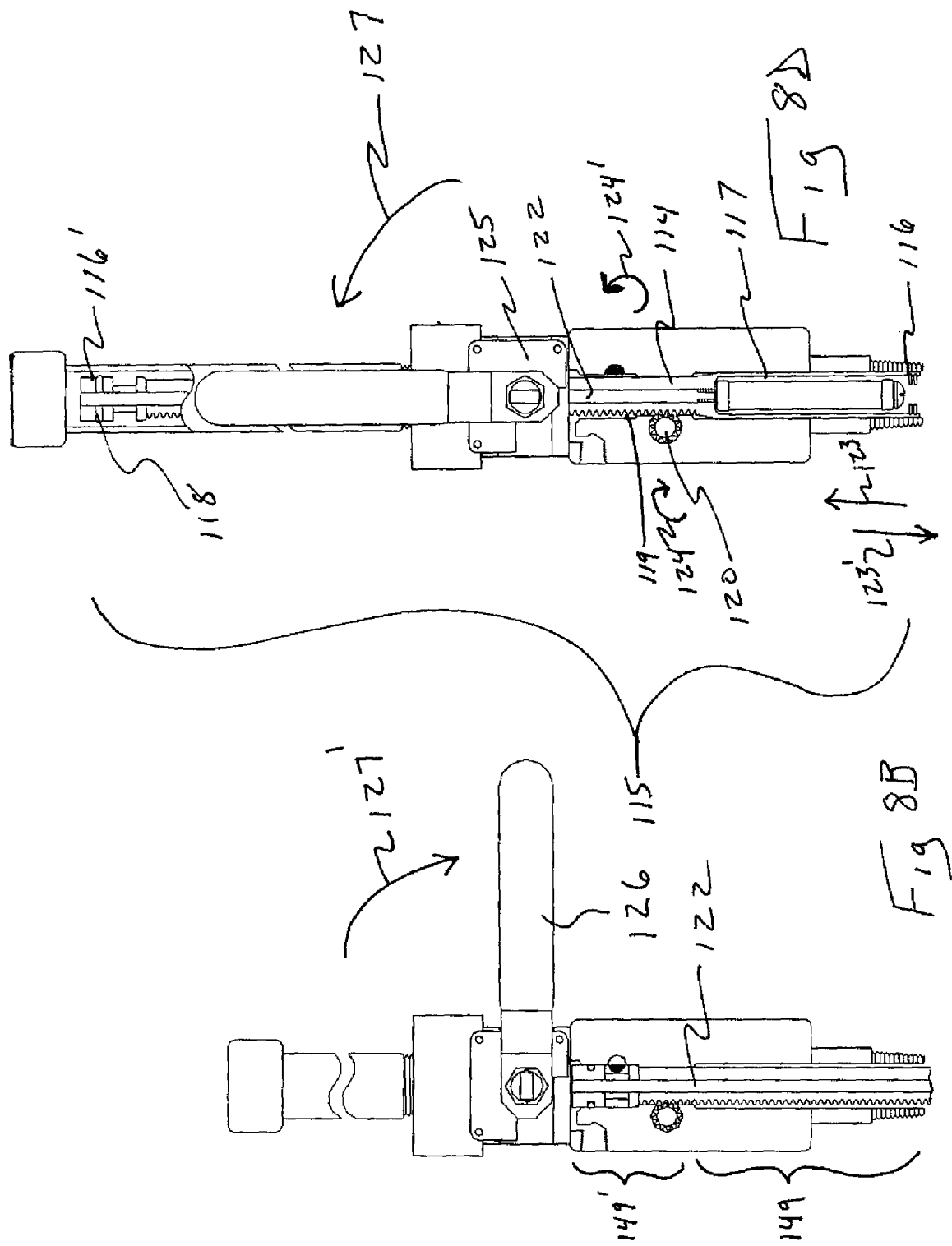

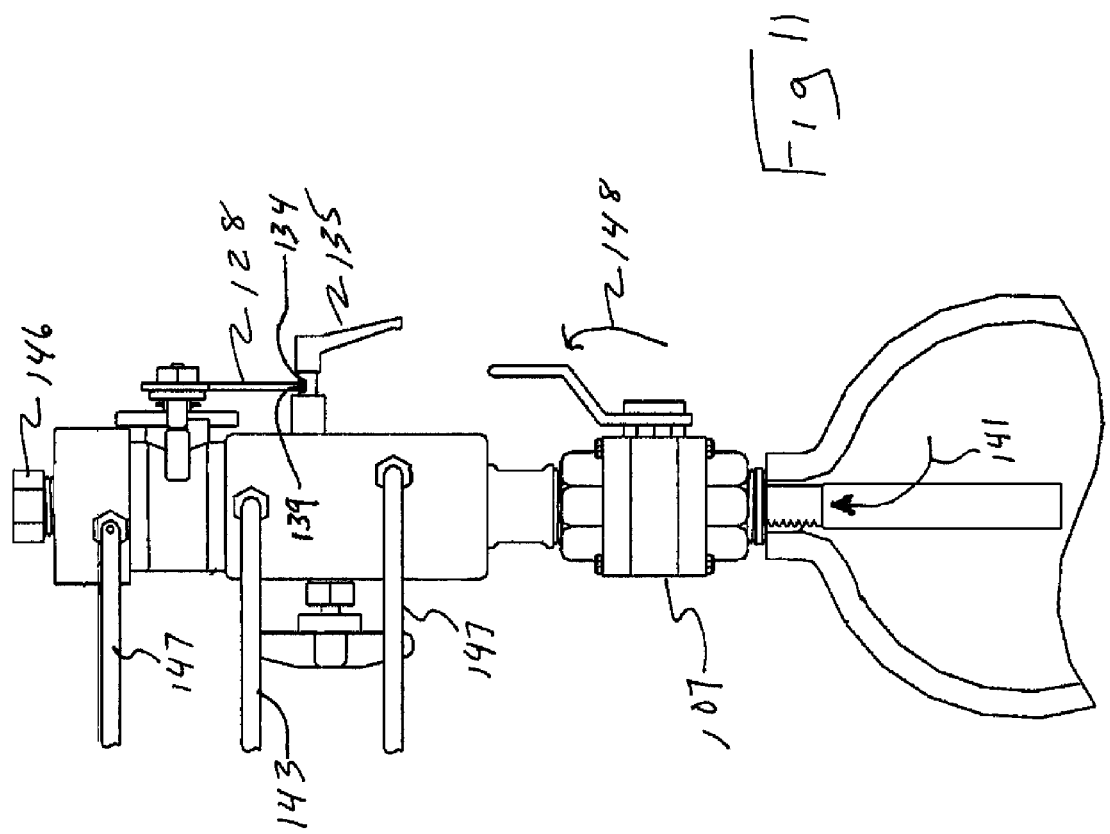

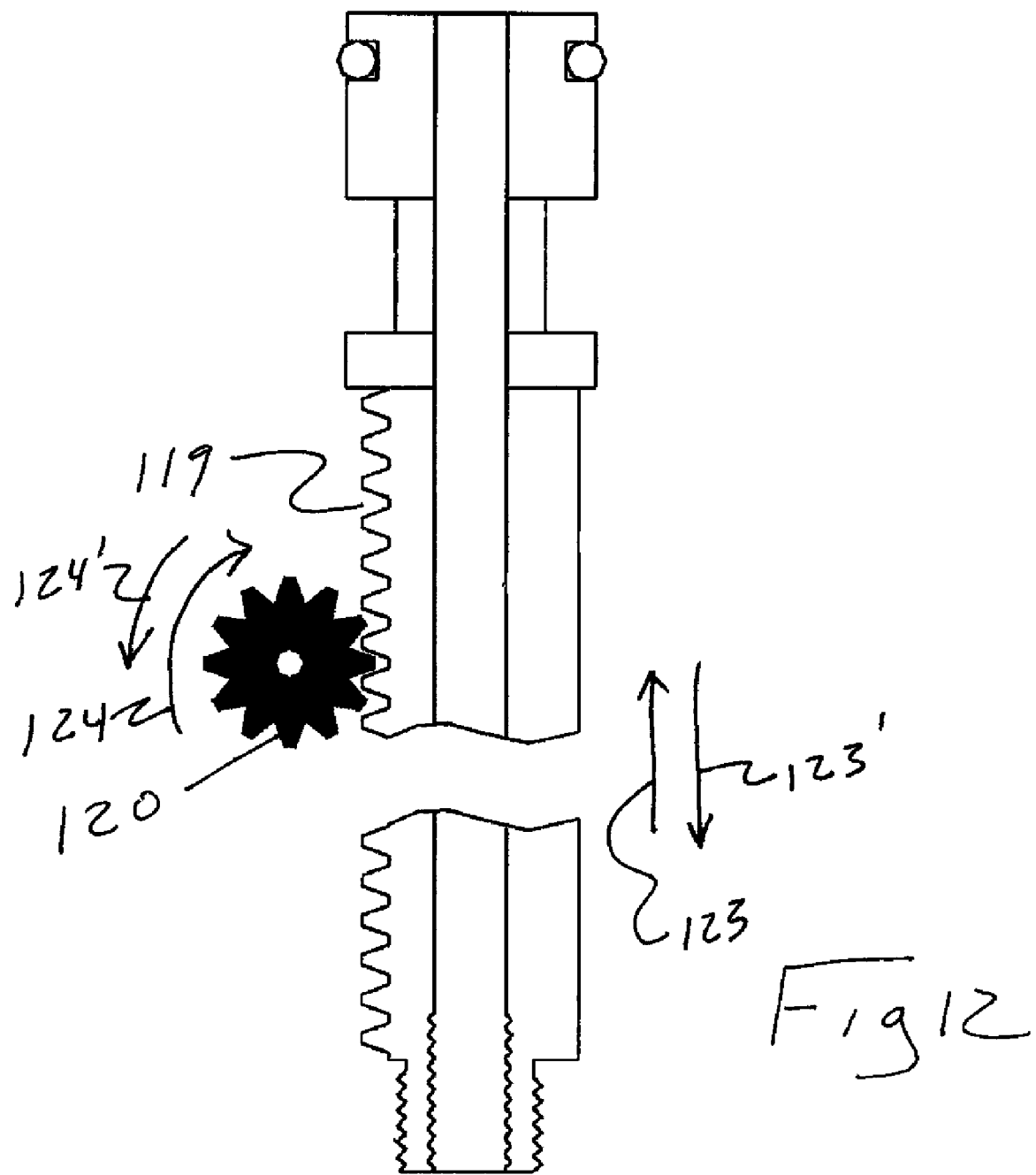

PORTABLE INSERTABLE PROBE ASSEMBLY INCLUDING HAZARDOUS OPERATIONS CAPABILITY

DOMESTIC PRIORITY DATA AS CLAIMED BY APPLICANT

The present application is a continuation in part of U.S. patent application Ser. No. 11/151,186 filed Jun. 13, 2005 now U.S. Pat. No. 7,472,615, which claims the benefit of Provisional Application 60/646,332 filed Jan. 24, 2005 entitled "Portable Insertable Probe Assembly".

TECHNICAL FIELD OF THE INVENTION

The present invention relates to the insertion of a probe into a pressurized process. Insertion of a probe into a pressurized process is often required for the purpose of extracting fluid samples, measuring fluid temperature, insertion of corrosion coupons and many other uses.

The preferred embodiment of the present invention contemplates a system configured to insert a probe though the sidewall of a containment vessel, whereas a pressure equalization technique is utilized in lieu of a probe packing gland or seal. Safety is improved by eliminating potential seal leaks. The length and size of the assembly is smaller than current means, the complexity of operation is reduced, and the overall cost for fabrication is reduced.

BACKGROUND OF THE INVENTION

The heating value of natural gas has a significant impact on its monetary value. In general, the heating value of natural gas increases as the concentration of low volatility, high molecular weight components increases. Condensation of gas phase components, which reduce the proportion of high molecular weight components, therefore tends to decrease gas phase heating value, while vaporization of entrained liquid has the opposite effect.

In order for natural gas supply to keep up with demand over the next 10 to 20 years, it will be necessary to increase production from deep-water fields in the Gulf of Mexico. (Refer to Volume 1, Fall/Winter 1997 official newsletter of Colorado Engineering Experiment Station Inc.) Gas produced from deep-water fields contains higher concentrations of low volatility components, such as water vapor and heavy hydrocarbons, and has a higher susceptibility to condensation than shelf and onshore production gas.

Additionally, some onshore produced gas, particularly in low ambient temperature regions, frequently contains entrained liquids. Other liquids, which can influence vapor phase composition when fluid pressure or temperature changes occur, include glycols and amines, which are carried over into the gas phase from gas contactors designed to remove water vapor and acid gases, respectively.

A Joint Industry Project (JIP) is underway to address problems associated with measurement and transportation of wet gases. A part of the JIP focus will include improvement of wet gas sampling techniques.

The American Petroleum Institute (API) and the Gas Processors Association (GPA) are two leading industry organizations, having recommended standard practices for sampling and analysis of natural gas.

Both of these organizations recommend the use of sample probes inserted into the process fluid, for the purpose of extracting samples of said process fluids. Further, both require that the probe be inserted to a specific depth in the containment vessel or pipeline. (Refer to Manual of Petroleum Measurement Standards chapter 14—Natural Gas fluids measurement, section 1 collecting and handling natural gas samples for custody transfer, fourth edition, August 1993.)

Insertion of probes into pressurized systems for collecting liquid samples is also a frequent requirement. The sample probe is generally the first element, as well as being a key component of a sample conditioning system. The accuracy of the fluid sample's compositional analysis can be impacted by the sample probes performance. The sample probe may provide an extracted sample which may be transported to a process analyzer or the like, but it may also be utilized to direct a sample into a cylinder (called "cylinder sampling") where the sample is container for later analyzation or other use.

The sample may be referenced as a "representative sample", however this does not always mean that all components of the sample stream are ultimately present for testing. Often "representative" can relate only to certain components of interest or phase. This is the case with Natural Gas process sampling, where a representative sample under industry standards is considered to be components in the gas phase. Thus, liquid is typically intentionally excluded at pipeline condition sampling. Also, applications where a liquid is entrained in a process gas in droplet form present other problems with regard to sample extraction representative of components of interest, as liquid droplets in the sample train can alter the composition of the gas phase, as when a combined gas/liquid sample stream undergoes pressure and/or temperature changes. If the desired representative sample is not accurately obtained, the analytical process is impacted.

Thus, it is advantageous under certain conditions to extract only the gas phase at the prevailing pressure and temperature of the source gas.

In many cases, the cost of installing a fixed probe at each sample location is cost prohibitive. For example, some pipeline companies sample fluids at several thousand locations. Outfitting each sample tap location could cost several million dollars. The result is that fluids are often sampled without the use of probes, which results in non-conformance of applicable standards, and inaccurate sample analysis.

It would be desirable, therefore, to have the capability of inserting a probe into the pressurized fluid systems at the time of sampling, (and preconditioning where desired) and retracting said probe upon the completion of the sampling process. To be effective, the probe insertion/retraction process must be safe, easy and quick to perform, portable, and effective for the intended service.

The same can be said for measuring the fluid temperature, wherein a temperature probe or well designed to receive a temperature probe is required to be inserted and/or retracted from a pressurized fluid stream or containment vessel. There is also a frequent need to insert other types of devices into pressurized system, such as the insertion/retraction of corrosion coupons, flow measuring devices and various types of sensors, analyzer, and devices.

Additionally, it is often desirable to retract a probe-type of device from a pressurized system to accommodate "pigging", or other type of maintenance operation.

Insertion and retraction devices for insertion/retraction of probe or probe like devices are known. However, they all employ a seal, through which the probe is inserted into the pressurized system, for the purpose of preventing pressurized fluid from leaking.

In these probes, the insertion force is derived either from a screw-type of device, or pneumatically or hydraulically. Such is the case with U.S. Pat. Nos. 4,177,676, 5,770,809, 5,639, 975 and 5,627,749. The apparatus of these aforementioned patents are bulky and long, requiring, at a minimum, a length of at least twice the maximum insertion length to extend above the point of insertion into a vessel. In many cases, such as in the tight quarters of a chemical plant, refinery, or offshore drilling platform, the bulk and length of these type devices preclude their use. Obviously, their design does not lend itself to rapid and safe insertion and retraction from a pressurized fluid source.

GENERAL SUMMARY OF INVENTION

Unlike the prior art, the present invention provides an assembly for insertion and retraction of a probe or probe-like device, with preconditioning capability, which does not require a seal or packing gland. For a given insertion/retraction length, the required insertable probe assembly length is considerably less than that of prior art devices, and since dynamic sealing of the probe which is known to leak fluids is not required with the present invention, safety is enhanced.

The preferred embodiment of the present invention contemplates pressure equalization between the pressurized process fluids and the housing containing a probe, so as to negate the use of a dynamic seal. In a first operating mode of the preferred embodiment of the present invention, the housing assembly, having a first and second end and containing the probe, has its first end attached, and in fluid communication with, the pressurized source fluid, through a full opening valve. Said attachment is by means of threads, flange, or other similar means.

Said valve is opened so as to allow fluid communication between the pressurized fluid source, and the interior of the housing assembly. Fluid flow will occur until the pressure of the housing assembly and the fluid source are equal to each other. The probe can now be lowered through an opening in the first end of said housing assembly without having to overcome the force exerted by the differential pressure across a dynamic seal, as is the case with prior art.

This allows for relatively simple means of inserting/retraction of the probe into and from the pressurized fluid. A preferred means of the preferred embodiment of the present invention for insertion/retraction is the use of the rack and pinion, wherein the rack in fabricated on the probe and the pinion, anchored in the housing assembly, is rotated manually.

In the preferred embodiment, the housing assembly has a first end attached and in fluid communication with the pressurized fluid source. When a first end of the probe is inserted into the pressurized fluid source, a second end of the probe remains within the housing assembly. In the preferred embodiment, a conduit having a first and second end is contained within the housing assembly.

The second end of said conduit is attached, and fluidly sealed to, the inner wall of the second end of said housing assembly. The inner diameter of the conduit is larger than the outer diameter of the probe. The first end of the probe extends inside the conduit. A sliding seal is established between the inner wall of the conduit and the outer wall of the probe. This allows the interior space of the probe and conduit to maintain fluid isolation with the space interior to the housing assembly, and exterior to the probe and conduit.

This arrangement of the probe and conduit provides a telescoping action, as the first end of the probe is inserted into, and retracted from, the pressurized process. Said sliding seal maintains a fluid seal between the outer wall of the probe and the inner wall of the conduit, during the telescoping process. The second end of said conduit is attached to, and fluidly sealed to, the interior wall of the second end of the housing assembly. An outlet port, permitting external fluid communication with the interior of the second end of said conduit, is formed in the second end of the housing assembly.

Therefore, when the probe housing assembly is attached to a pressurized fluid pressure source through a fully opening valve, the probe can be manually inserted to a desired depth in the pressurized fluid source, thereby providing a fluid path between said pressurized source and said outlet port.

It should be noted that since a seal does not exist between the outer probe wall and the interior wall of the housing assembly, the pressure internal to the housing assembly, but external to the probe and conduit, is essentially the same as the static pressure of the pressurized fluid source.

It should also be noted that the internal pressure of the probe and conduit are also essentially the same, as the static pressure of the pressurized fluid source, with only a slight difference existing whenever fluid flow through the probe and conduit cause a slight pressure drop.

The differential pressure across said sliding seal is minimal. In a second embodiment, fluid communication between the second end of the probe and the outlet port is by way of a flexible conduit attached to and in fluid communication between the second end of said probe and said outlet port. In this second embodiment, the conduit and sliding seal are eliminated.

In the preferred embodiment, by closing off the first end of said probe, a well is formed interior to the probe, with the conduit extending from the outlet port to the first end of said probe. Said well can be at atmospheric pressure when the outlet port is opened to the atmosphere, and can therefore be utilized for several purposes, such as, for inserting a temperature sensor inside of the pressurized fluid source.

Other minor variations obvious to one skilled in the art are also possible, such as insertion/retraction of corrosion coupons, or various sensors inside of the pressurized fluid process. Another variation of the preferred embodiment of the probe housing assembly is for the first end of the probe to slide over the first end of the conduit, wherein the sliding seal is formed between the inner wall of the first end of the probe, and the outer wall of the conduit.

Another embodiment of the present invention contemplates a hazardous operation sample probe (hereinafter referred to as the "Hazop Probe") is configured for safe and rapid insertion which may include preconditioning elements in the sample probe, utilizing a secondary valve for employing the pressure balance technique. The Hazop Probe embodiment is specifically designed for use at high pressures, and unlike the prior art, this device requires no separate external insertion/retraction devices, and thus does not entail ramming the probe through a seal. The pressure balance technique in the present system is made possible through the utilization of an external housing containing the probe, which housing is pressurized by the process.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 8 is a front, partially cut-away view of an embodiment of the invention suitable for insertion/retraction of the sample probe under high pressure, hazardous operation conditions, hereinafter referred to as the "hazop probe", which further includes a secondary, upper valve (the "hazop valve") to selectively seal the passage to the probe housing, as well as other features herein discussed, the hazop probe embodiment shown mounted to a process sample valve leading to a pressurized process stream.

FIG. 8B is a side, partially cut-away view of the hazop probe of FIG. 8A, illustrating the hazop valve in closed position with the probe sealed off from the housing, the upper portion of the probe having been lowered through the hazop valve.

FIG. 8D is a side, partially cut-away view of the hazop probe of FIG. 8C, illustrating the hazop probe in open position so that the upper portion of the probe is raised into the housing, so that the lower portion of the probe is removed from the process stream.

FIG. 11 is a side view of the invention of FIG. 8 with showing the hazop valve in a closed position, the rack handle in a locked position, the housing removed with the connection plugged, the lower portion of the probe shown in the process stream, and vent and sample conduits engaging the vent and sample ports.

FIG. 12 illustrates a view of the rack and pinion drive for lowering and raising the sample probe in the system.

FIG. 17 is an isometric, side view of the probe assembly mounted to a valve mounted to a pipe containing a pressurized process gas or the like.

DETAILED DISCUSSION OF THE INVENTION

Figure 1:
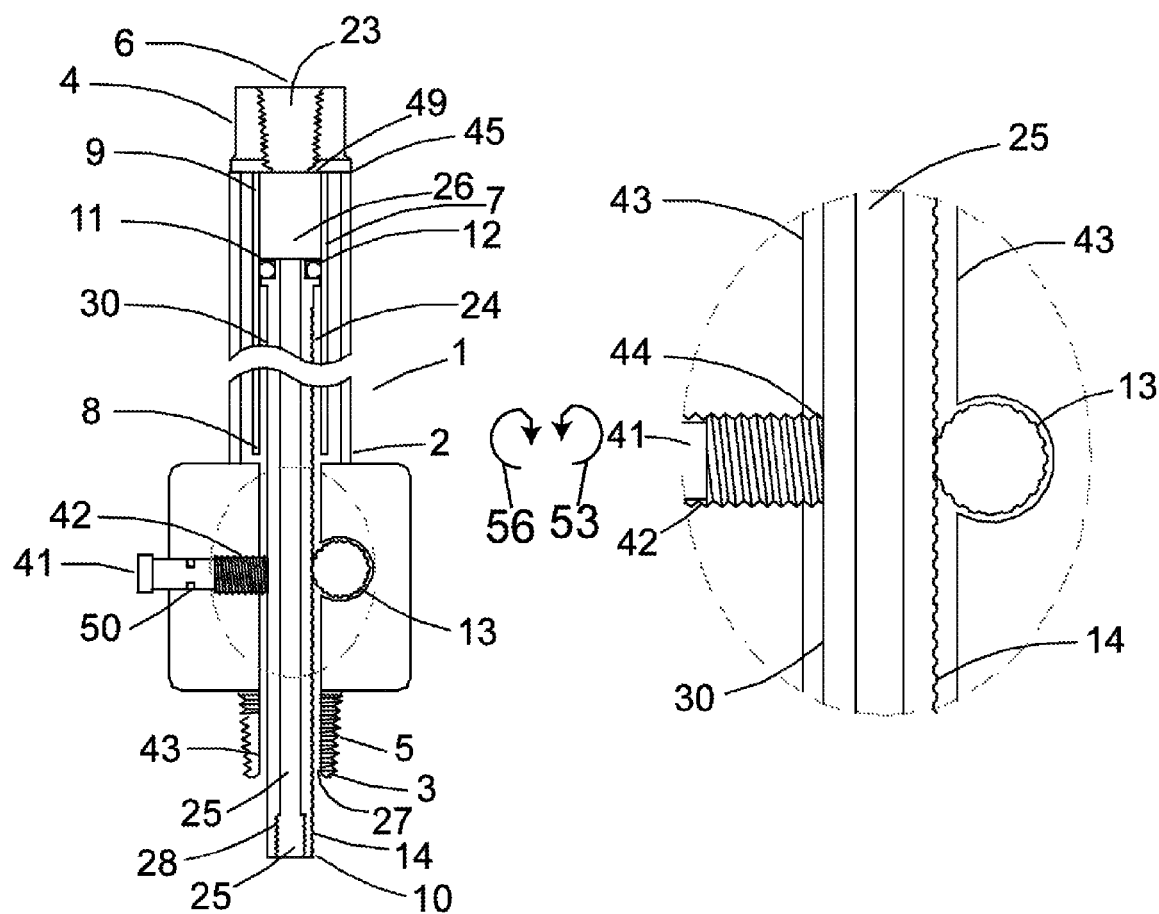
FIG. 1 is a side, partially cut-away view of the preferred first embodiment of the invention illustrating the probe house assembly.
Figure 2:
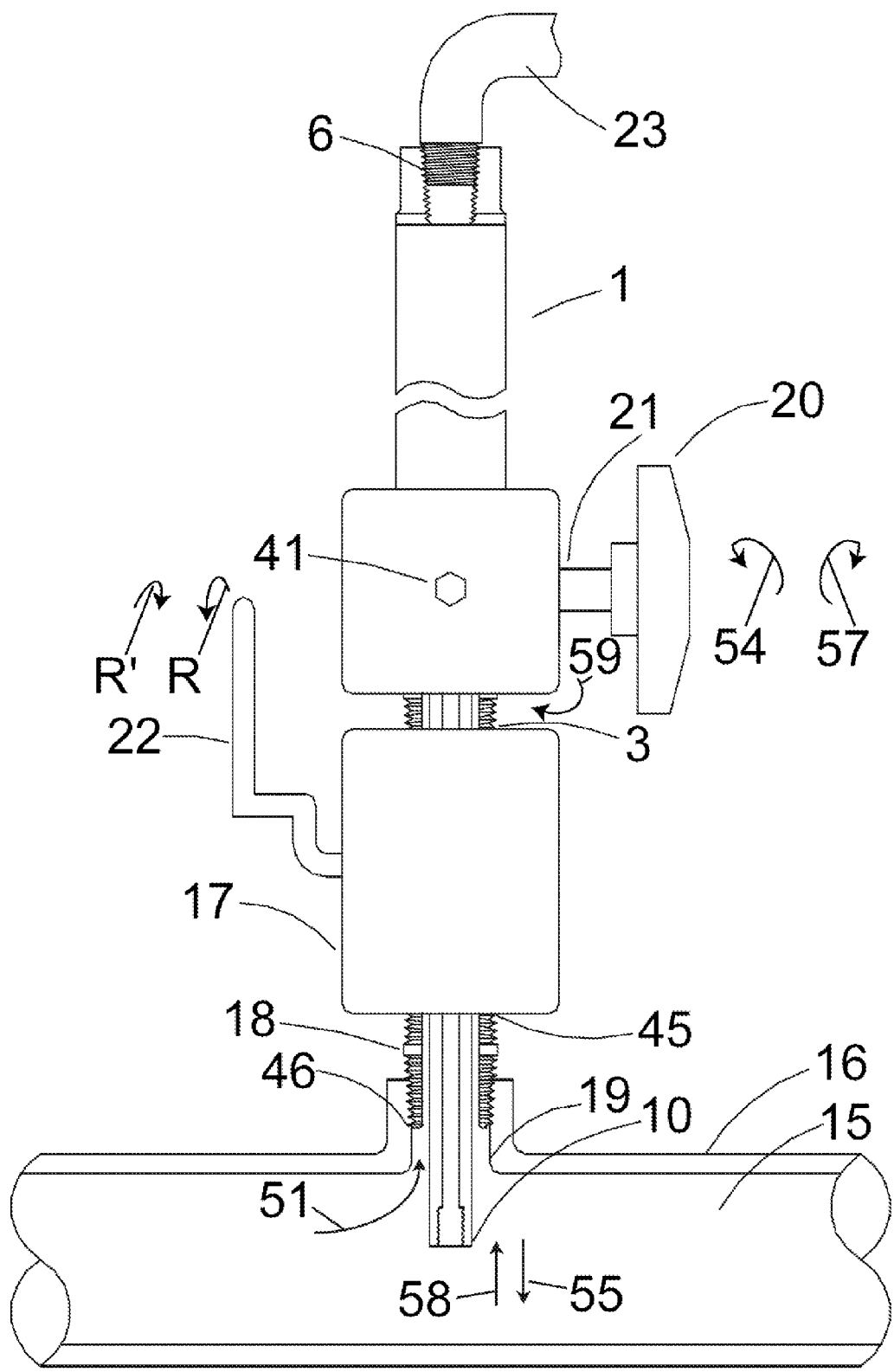
FIG. 2 is a side, partially cut-away view of the preferred first embodiment of FIG. 1 in an exemplary installation.

Referring to FIGS. 1 and 2, the preferred first embodiment of the invention contemplates a probe housing assembly 1 comprising a probe 30, conduit 7, and housing assembly 2. Cavity A 24, formed within housing assembly 2, extends longitudinally from the first end 3 of housing assembly 2 to the second end 4 of housing assembly 2. Cavity A 24 is formed between the inner wall 43 of housing assembly 2, and is external to conduit 7. Threaded outlet port 6 is formed in the second end 4 of housing assembly 2, and male N.P.T. threads 5 are formed in first end 3 of housing assembly 2.

The second end 9 of conduit 7 is attached and fluidly sealed to the inner wall 49 of the second end 4 of housing assembly 2. The first end 8 of conduit 7 extends into cavity A 24. Sliding seal 12 is formed on second end 11 of probe 30, said second end 11 of probe 30 being inserted into the open end of first end 8 of conduit 7, said sliding seal 12 providing fluid seal between the outer wall of second end 11 of probe 30 and the inner wall of conduit 7.

A rack gear 14 on probe 30 extends from first end 10 of probe 30 to second end 11 of probe 30, said rack gear 14 mechanically engaged with pinion gear 13 associated with housing 2. Said pinion gear 13 having a pinion gear shaft 21 and pinion gear handle 20 formed to provide an external means for mechanically rotating said pinion gear 13.

Probe travel locking screw 41 thready engaged in threaded opening 42 provides a means for locking probe 30 at a desired protrusion length, by selectively rotating the screw to engage or disengage said probe. Seal 50 provides a seal between the atmosphere and the pressure fluid process. Fluid communication passage 23 is established between the first end 10 of probe 30 and threaded outlet port 6, said fluid path comprising of passage A 25, formed internal to probe 30 and passage B 26, formed internal to conduit 7.

Said fluid path is formed to be capable of providing a fluid flow from pressurized fluid process 15 to an external device fluidly attached to threaded outlet port 6. The function of the preferred, first embodiment of the invention is to extract a sample of fluid from a pressurized fluid process 15.

In operation of the preferred first embodiment of invention, probe housing assembly 1 is attached to a fully opening valve 17 by way of male N.P.T. threads 5, said fully opening valve 17 being attached to a first end 45 of nipple 18 and second end 46 of nipple 18 being threadingly attached to pipe or vessel 16. An opening 19 formed in the wall of the pipe or vessel 16 provides fluid communication between nipple 18 and pressurized fluid process 15.

After probe housing assembly 1 is attached to fully opening valve 17 as previously described, said fully opening valve 17 is manually opened by rotating R valve handle 22 wherein a small volume of fluid from pressurized fluid process 15 flows 51 through opening in wall of pipe or vessel 19, annulus 27 and into cavity A 24 until its fluid pressure in cavity A 24 is equal to that of the pressurized fluid process 15. Rotating 53 first end 44 of probe travel locking screw 41 in a counter-clockwise manner will disengage probe travel locking screw from probe, and release probe 30.

Rotating pinion gear handle counterclockwise 54 will extend 55 probe 30 out of housing assembly 2. In this manner probe 30 can be extended through fully opening valve 17, nipple 18, opening in wall pipe or vessel 19 and into pressurized fluid process 15. When first end 10 of probe 30 is extended to the desired depth in pressurized fluid process 15, rotating 56 probe travel locking screw 41 in a clockwise manner until it is securely against probe 30 will engage and lock said probe 30 in that position. During the extension of probe 30, sliding seal 12 maintains a fluid seal between cavity A 24 and passages A 25 and passage B 26.

To detach the probe housing assembly from the fully opening valve 17, one must first unlock probe 30 by turning or rotating 53 probe travel locking screw 41 counter-clockwise to disengage, rotate 57 pinion gear handle 20 clockwise until probe 30 is fully retracted 58 into housing assembly 2, turning or rotating 56 probe travel locking screw 41 clockwise to engage and lock probe 30 in place, rotate R' valve handle 22 clockwise until fully opening valve 17 is fully closed then unscrewing 59 male N.P.T. threads 5 from the body of fully opening valve 17.

The rack and pinion drive illustrated and discussed is only an example of various means which can be implemented to selectively extend and retract the probe from the housing assembly. A friction drive comprising, for example, a friction wheel rotatingly mounted to the housing and frictionally engaging the probe may likewise be utilized with a handle for selective rotation of the wheel, much in the manner discussed above, could likewise be utilized with good results. Other alternatives could include, for example, magnetic means in the form or electromagnets, rare earth magnets, or the like mounted to the housing or probe to facilitate the selective extension or retraction of the probe from the housing assembly.

Figure 7:
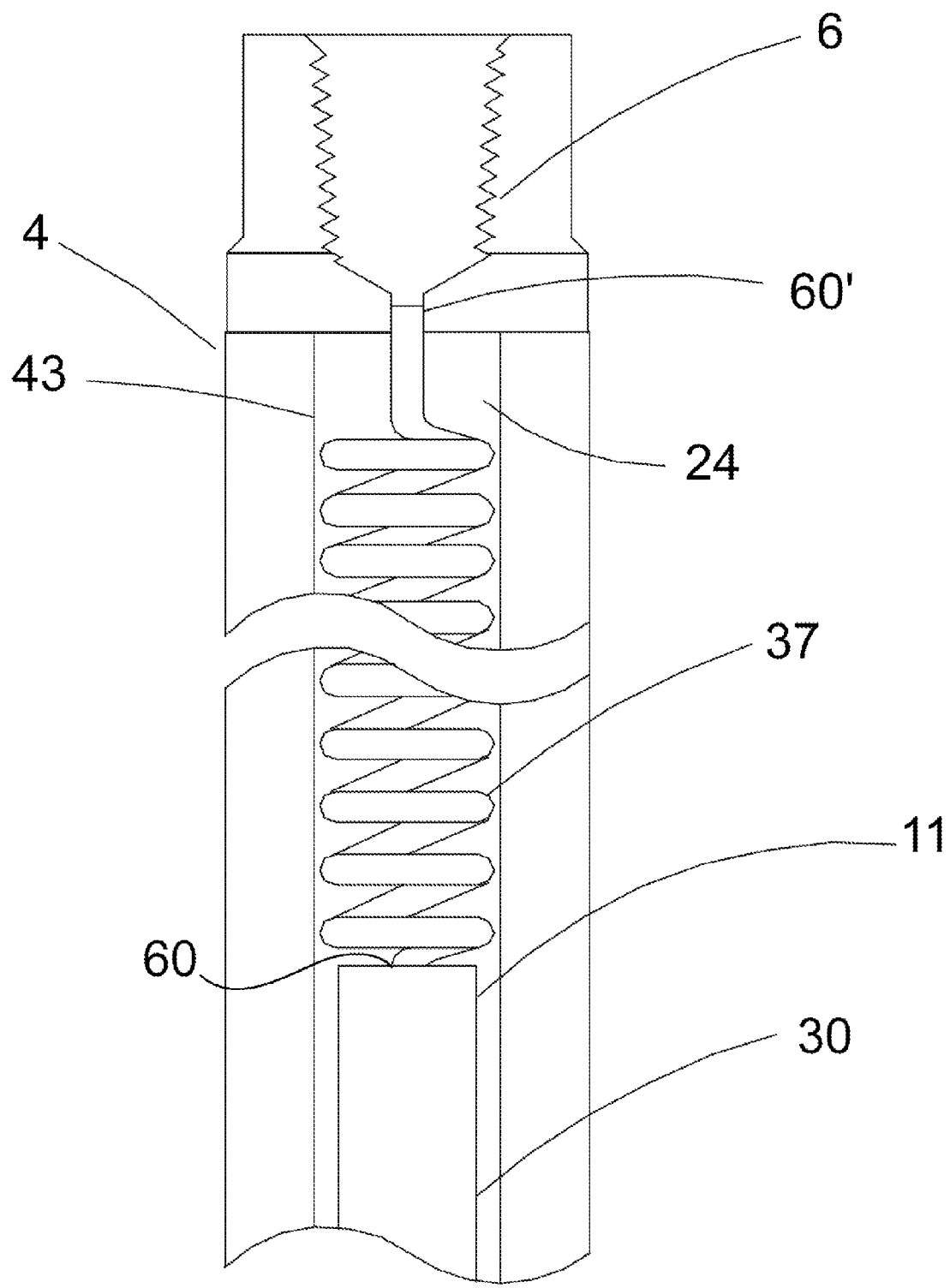
FIG. 7 is a side, partially cut-away view of a second embodiment of the invention, wherein there is shown a flexible conduit for sample fluid extraction from the pressurized fluid process.

In preferred second embodiment of the invention (Refer to FIG. 7), a flexible tube or conduit 37 having first 60 and second 60' ends, shown in a helical coiled configuration, engages the second end 11 of probe and outlet port 6, respectively, to provide fluid communication therebetween. The operation of probe housing assembly 1, for extracting a pressurized fluid process 15 sample, is essentially the same as that of the aforementioned preferred first embodiment.

Figure 3:
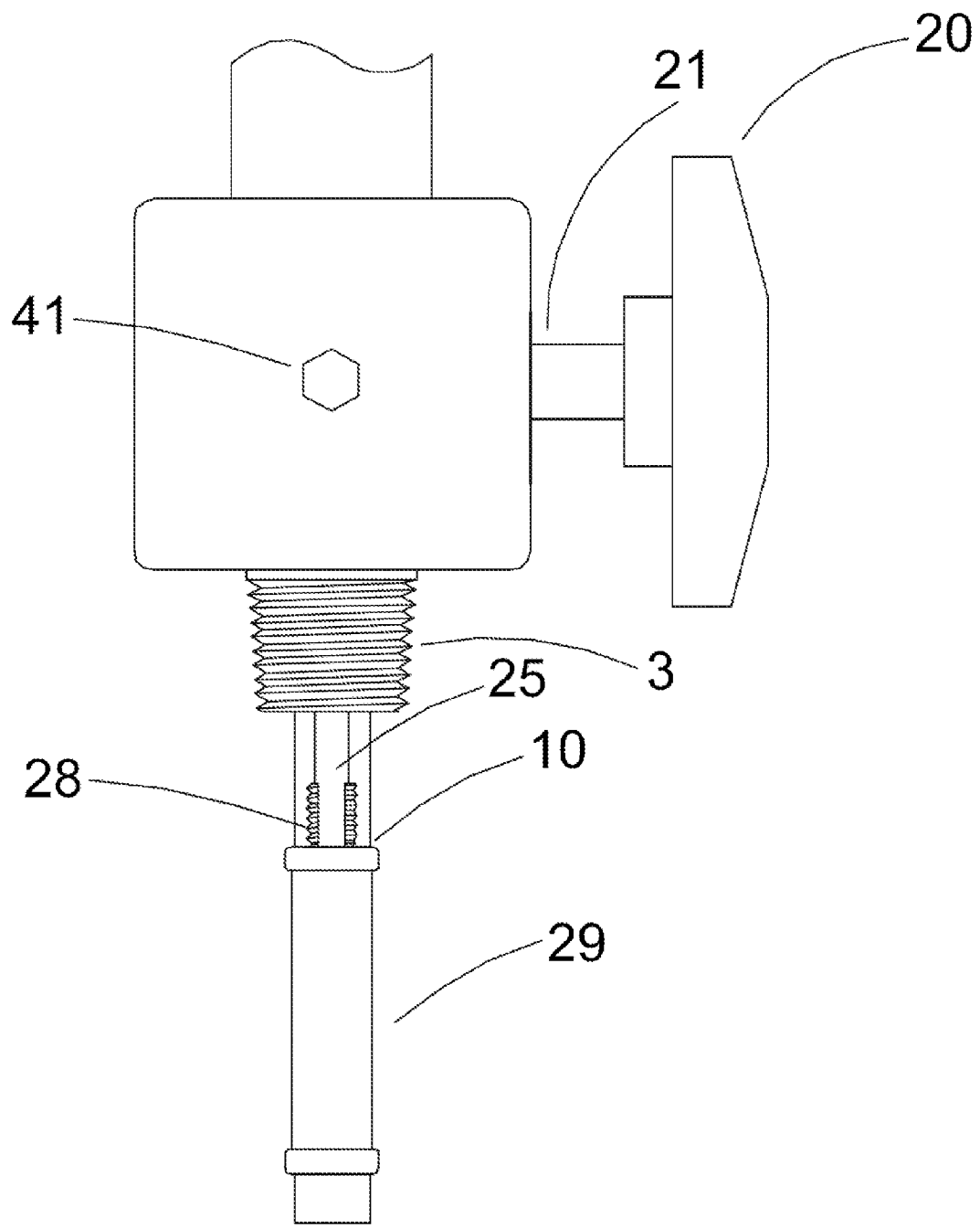
FIG. 3 is a side, partially cut-away view of a third embodiment of the present invention incorporating a phase separating membrane/filter assembly.

In a preferred third embodiment of the invention (Refer to FIG. 3), a phase separating membrane/filter assembly 29 is attached to threaded opening 28 to passage A 25, said phase separating membrane/filter assembly 29 rejecting liquid and solid particles while allowing the passage of gas or vapors into passage A 25. Operation of said third embodiment is essentially as that of first embodiment.

Figure 4:
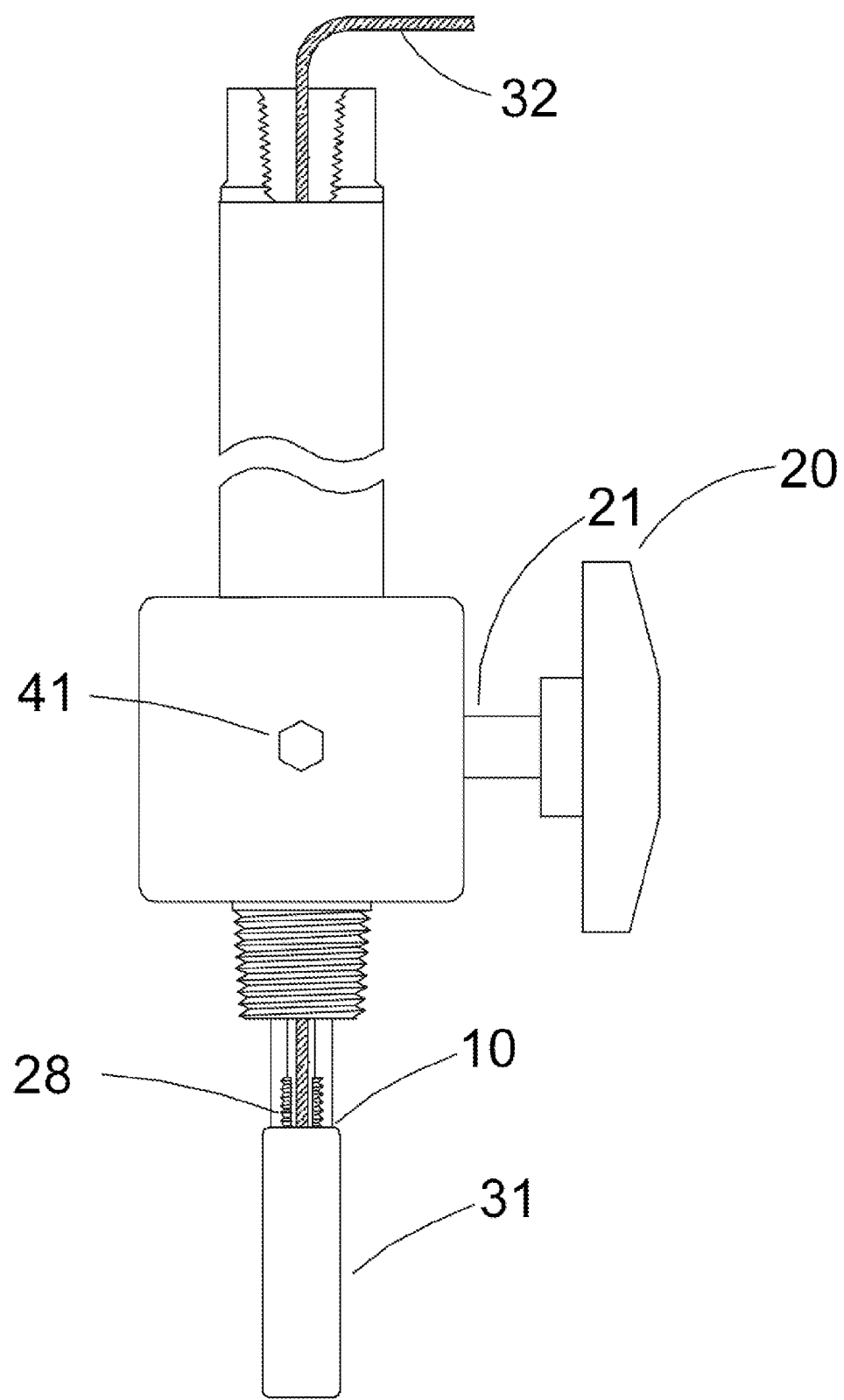
FIG. 4 is a side, partially cut-away view of a fourth embodiment of the present invention, incorporating a sensor for selectively engaging the pressurized fluid process.

In a preferred fourth embodiment of the invention (Refer to FIG. 4) a sensor 31 is attached to threaded opening 28 to passage A25, said sensor 31 having communication cable 32 extending through passage A 25, passage B, and outlet port 6. Operation for extending sensor 31 into pressurized fluid process 15 is essentially the same as for preferred first embodiment.

Figure 5:
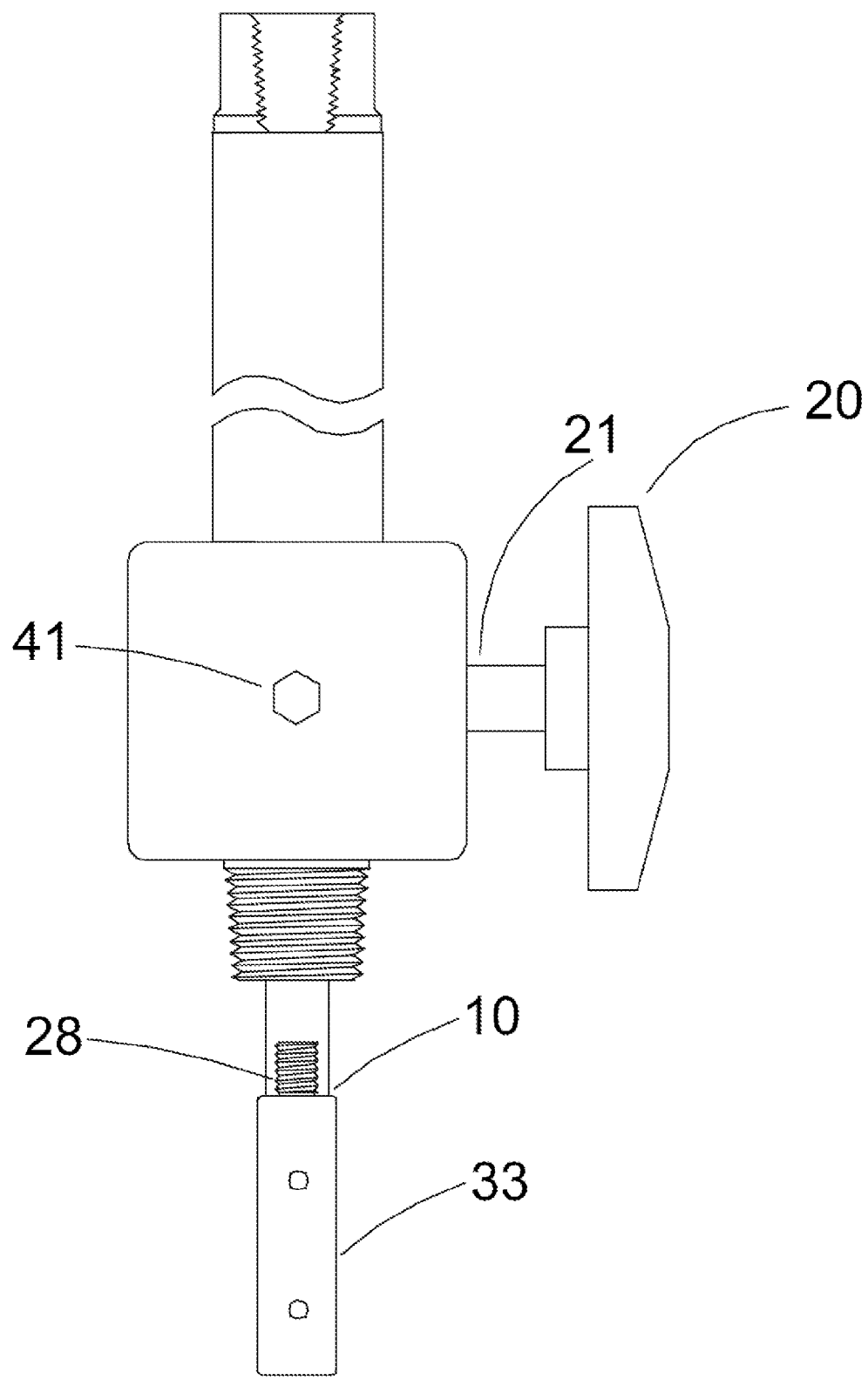
FIG. 5 is a side, partially cut-away view of a fifth embodiment of the present invention wherein there is provided an attachment plate engaging a corrosion coupon for selectively engaging the pressurized fluid process.

In a preferred fifth embodiment shown in FIG. 5 attachment plate for corrosion coupon 33 is attached to threaded opening 28 to passage A 25 which can then be inserted into a pressurized fluid process 15 in a manner similar to that described for first preferred embodiment.

Figure 6:
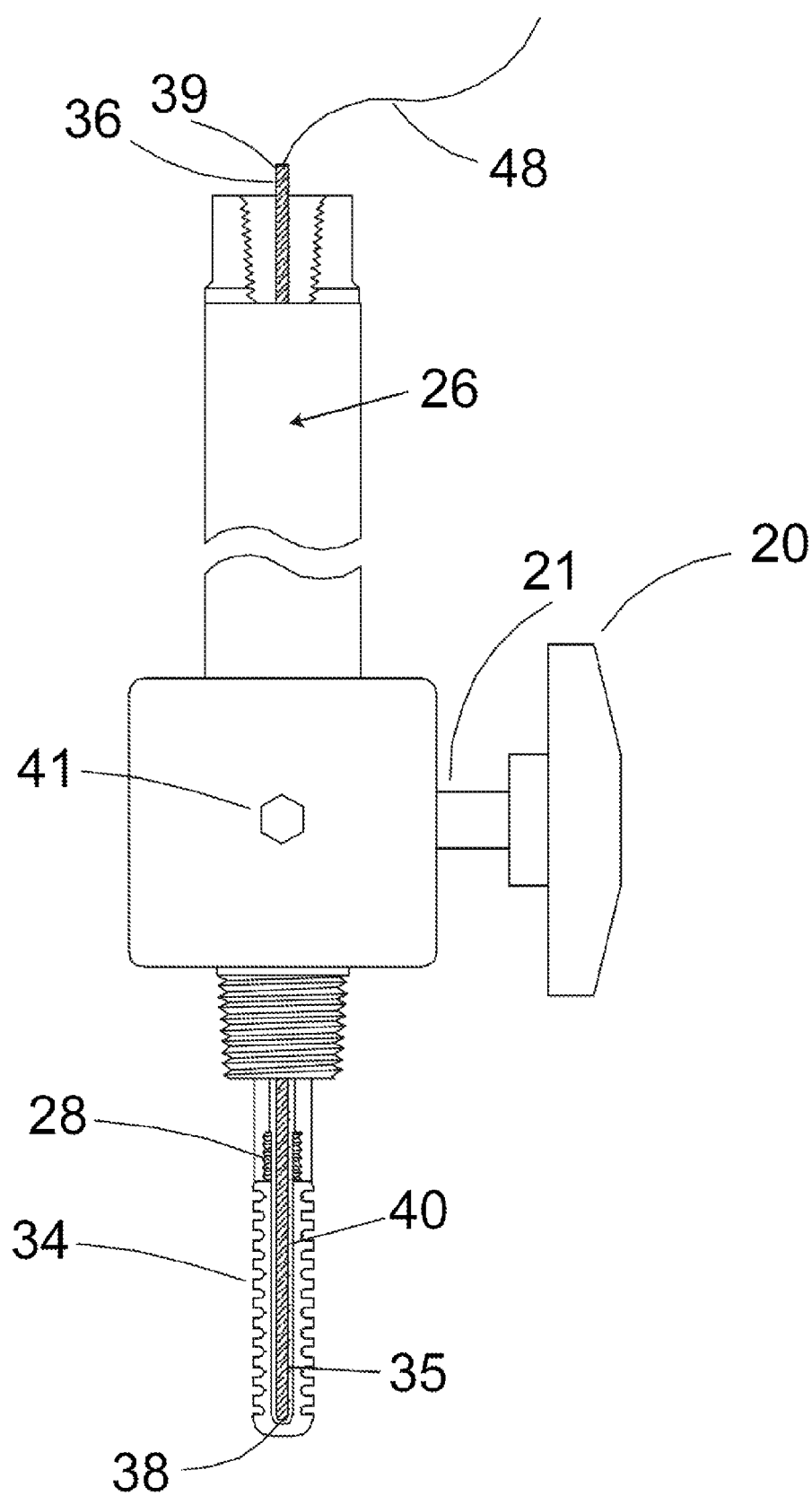
FIG. 6 is a side, partially cut-away view of a sixth embodiment of the invention wherein there is provided a well for receiving a temperature sensor or other object for lowering into a monitoring area.

In a sixth preferred embodiment (Refer to FIG. 6) a closed end cap 34 having a finned outer surface 40 is attached to threaded opening 28 to passage A 25 which effectively seals off said threaded opening 28 to passage A.

Thus, a well is formed, comprised of closed end cap well 35, passage A 25, passage B 26, and threaded outlet port 6. A temperature sensor 36 or other similar object can now be lowered (at its first end 38) into the closed end cap well 35, which remains open to the atmosphere even when probe 30 is extended into pressurized fluid process 15. A temperature sensor cable 48 relays the signal from the probe at the second end 39 of the temperature sensor 36. Operation of this sixth preferred embodiment is similar to that of the preferred first embodiment. The fins facilitate thermal transfer from said pressurized fluid process to said sensor in said well.

In summary, a method engaging a pressurized fluid system with a probe utilizing the preferred embodiment of the present invention may be summarized as follows:

a. providing a probe housing assembly for insertion and retraction of a probe into a pressurized vessel, comprising:
- a telescoping probe having first and second ends, said telescoping probe having an internal fluid passage formed therethrough extending from said first end of said telescoping probe to said second end of said telescoping probe;
- a housing having first and second ends, said housing having an internal cavity formed therethrough extending from said first end of said housing to said second end of said housing, said housing formed to engage, in a fluidly sealed manner, a pressurized fluid process in said pressurized vessel;
- said telescoping probe slidingly disposed in said internal cavity formed in said housing in an approximate coaxial relationship with said housing, such that said second end of said telescoping probe can engage, in a fluidly sealed manner, said second end of said housing;

b. engaging said first end of said housing to valve engaging a pressurized vessel containing a pressurized fluid process;

c. opening said valve, providing an opening;

d. allowing said pressurized fluid process to selectively pass through said opening in said valve and into said internal cavity formed in said housing;

e. extending said first end of said probe from said housing, through said open valve, into said pressure vessel, such that said first end of said probe engages said pressurized fluid process;

f. retracting said probe into said housing, and g. closing said valve.

With the above process, a fluid sample can be obtained or other function accomplished, including, for example:

utilizing the fourth embodiment of the invention, mounting a sensor to said first end of said probe would allow one to expose said sensor to said pressurized fluid process in step "e".

utilizing the sixth embodiment of the invention, mounting a closed end cap having a cavity to said first end of said probe such that said cavity of said closed end cap communicates with said passage formed in said probe, to provide a well, would allow one, in step "e: to lower a sensor into said well while said well remains at atmospheric pressure with said probe engaging said pressurized vessel to seal said well from said pressurized fluid process, allowing said sensor to analyze said pressurized fluid process, while remaining at atmospheric pressure.

utilizing the preferred embodiment of the present invention, in step "e" one could allow said pressurized fluid process to flow into said conduit formed in said probe, sampling said pressurized fluid process, providing sampled fluid.

utilizing the second embodiment of the invention, in step "e", one could utilize direct said sampled fluid through said flexible conduit, through the outlet port of said housing assembly, for collection.

utilizing the third embodiment of the present invention, in step "e" one could utilize said phase separating membrane/filter assembly to engage said pressurized process fluid such that gas flows through said phase separating membrane/filter assembly into said conduit formed in said probe, while rejecting liquid and solid particles flowing through said pressurized process fluid, and utilizing the fifth embodiment of the present invention, in step "e", one could expose said corrosion coupon to said pressurized fluid process, for analysis of same.

A seventh embodiment of the present invention is illustrated on FIGS. 8-11, said embodiment being particularly suitable for hazardous operations, and hereinafter referred to as the "Hazop" probe. Continuing with FIG. 8, the Hazop probe incorporates important elements of the above cited embodiments of invention, including, for example, regard to the insertion and retraction of the probe into a pressurized fluid process utilizing a pressure balancing technique.

Like the embodiments of the invention illustrated in FIGS. 1-7, the Hazop Probe does not require a seal or packing gland, utilizing pressure equalization between the pressurized process fluids and the housing containing the probe, so as to negate the use of a dynamic seal. Like the above embodiments, the Hazop Probe embodiment utilizes an insertion/retraction mechanism for raising and lowering the probe, in the form of a linear rack with pinion mechanism.

Further, like the previous embodiments, the present Hazop probe embodiment is mounted to a valve to selectively allow fluid communication between the pressurized fluid source and the interior of the housing assembly to provide pressure equalization, with the probe able to be lowered through the opened valve into the pressurized fluid process.

Figure 8C:
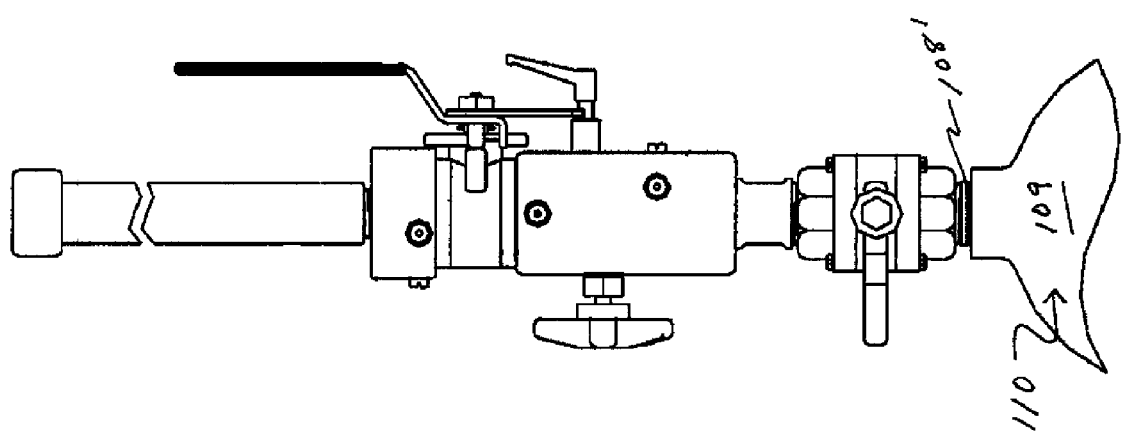
FIG. 8C is a front, view of the hazop probe of FIG. 8, illustrating the hazop valve in an open position so that the upper portion of the probe may be raised to be enclosed in the housing, the lower portion of the probe raised out of the process stream and sealed by the process sample valve, shown in the closed position.
Figure 8A:
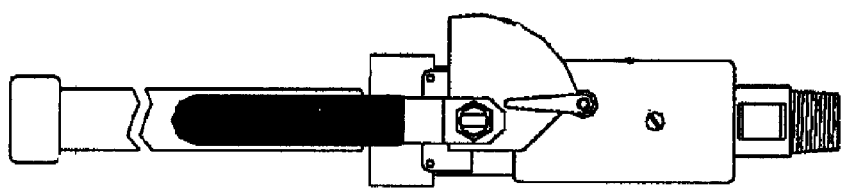
FIG. 8A is a side view of the hazop probe of FIG. 8, illustrating the hazop valve in the open position, so as to allow the passage of the probe therethrough.

As shown in FIGS. 8-8D and FIG. 12, the Hazop probe embodiment of the present invention comprises a probe assembly 101 having first 102 and second 102' ends (with a body 138 therebetween) and a length 103, the probe assembly shown having a conduit 104 formed through the length thereof having an interior diameter 105, and threaded connections 106, 106' at each opposing end 102, 102'.

First end 102 of the probe assembly is formed to engage, via threaded connection 106 (for example, via ¾" N.P.T.), the first end 108 of a valve 107 or the like, the second end 108' of the ball valve threadingly engaging a pipe or vessel 109 containing a pressurized fluid process 110 (FIG. 8C).

A tubular housing 111 is provided having first 112 and second 112' ends, the first end 112 being threaded 113 to engage said threaded connection 106' at said second end 102' of said probe assembly. The tubular housing has a conduit 104' formed along its length and, when connected to the probe assembly, provides an enclosure effectively extending the conduit 104 formed through the probe assembly 101.

Conduits 104, 104' are formed in the probe assembly and tubular housing to enclose a probe 114 having first 116 and second 116' ends and a length 115, the first end 116 forming the probe tip 117, which can readily engage various apparatus including phase separation membranes, etc, as discussed in the previous embodiments supra.

The second end is shown having situated thereabout an o-ring 118 which slidingly engages the inner diameter 105 of the upper portion 149' of conduit 104 in fluidly sealed manner. The probe has a conduit 122 running its entire length, from the probe tip to the second end 116'. As shown, the conduit 104 may have a lower portion 149 and an upper portion 149', with the upper portion having an inner diameter to slidingly engage the o-ring 118 on the probe for a fluid tight seal, as discussed, with the lower portion 149 having a larger inner diameter to accommodate the probe tip 117 and any apparatus affixed thereto.

A linear gear rack 119 is formed along at least a portion of the length 115 of the probe for longitudinally adjusting the position of the probe 114, the rack formed to engage a rotatable pinion gear 120, a portion of which is situated in conduit 104, which pinion gear is driven by a pinion gear handle 121 or crank knob, located exterior the probe assembly, and mounted at the body 138 of the probe assembly. The rack 119 and pinion 120 combination is formed to longitudinally position the probe tip 117 into 123' the lower portion 149 of conduit 104, in a retracted position, or out of 123 the conduit 104, in a deployed position, via rotation 124', 124 of the pinion gear 120 via pinion gear handle 121, respectively.

Also mounted to the probe assembly 101 is a ball valve (hereinafter hazop valve 125) formed to selectively provide an opening longitudinally aligned with the probe assembly conduit 104 to the tubular housing conduit 104', or which, when closed, seals off said second end 102' of said probe assembly conduit 104. The ball valve forming the hazop valve 125 should have an inner diameter sufficient to effectively extend the probe assembly conduit 104. A hazop valve control handle 126 is provided to selectively open 127 or close 127', the valve.

It is noted that the tubular housing 111 can vary significantly in length to accommodate most probe lengths, which can vary depending upon the installation and application. More specifically, in some applications, it may be advantageous to utilize an intermediary pipe between the second end 108' of the valve 107 and the threaded connection for pipe or vessel 109 containing pressurized fluid process 110. Such may be the case, for example, where the pipe or vessel 109 is situated below ground several feet, in which case an intermediary pipe running from the pipe or vessel 109 to ground level, which then engages the valve 107, can be provided to facilitate accessibility to the system. In such an application, the probe would have to have a length to accommodate the intermediary pipe, and the tubular housing 111 would likewise have to have a length adequate to accommodate the extended probe length. Thus, the probe length can vary significantly depending upon application.

It is also noted that, although the present embodiment illustrates the probe assembly and the tubular housing 111 as being separate components, it should be understood that this is an example of a design of the present invention and that the tubular housing and probe assembly, when engaged, can work as a single housing for the probe. Thus, the present example is not intended to be limiting as to the structure of the housing, and the present invention may accordingly practiced with a single housing having the entire length of the probe conduits 104, 104' therein.

Continuing with FIGS. 8, 8C, 9A-9D, and 10A-10D and 11, a rack lock apparatus 129 in the form of a rod 130 having first 131 and second 131' ends, the first end 131 having a half cylinder configuration to form a lock pin 132 is provided. The lock pin 132 is situated within the probe assembly 101 so as to selectively engage 136 or disengage 136',114, via rotation 137, 137' of the rod 130, a lateral slot formed 133 formed in the surface of the probe. The lock pin of the present embodiment performs a similar function to the locking screw of the first embodiment of the invention, that is, locking the probe in a desired position to render same immoveable (when locked).

Figure 10B:
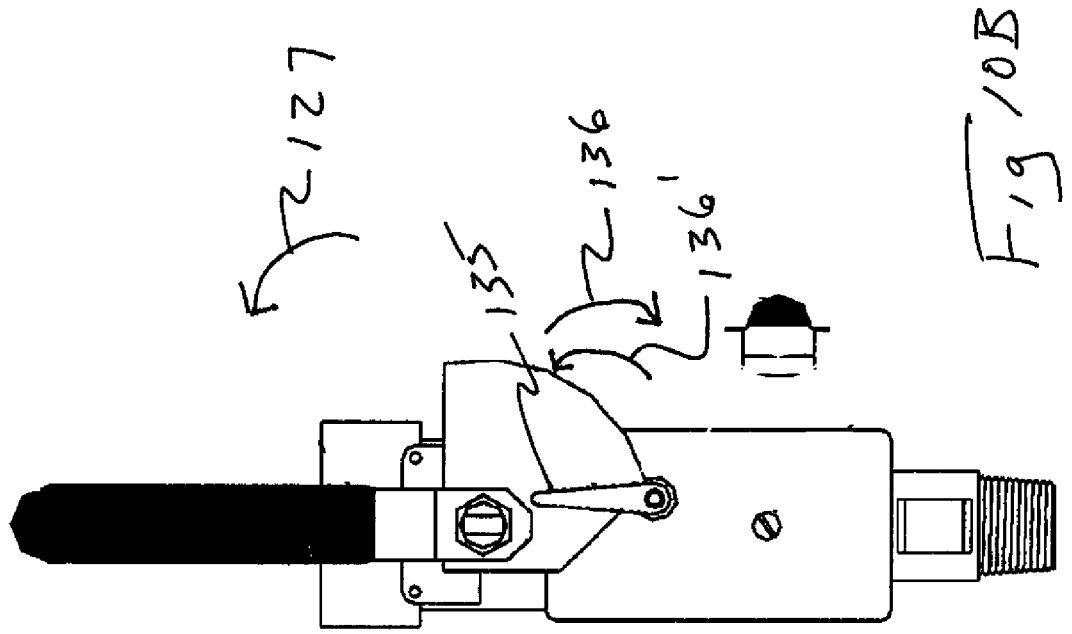
FIG. 10B is an opposite side view of the invention of FIG. 9B, illustrating the operation of the lock plate associated with the hazop handle, and showing the rack lock handle shown in the unlocked, operable position.
Figure 10A:
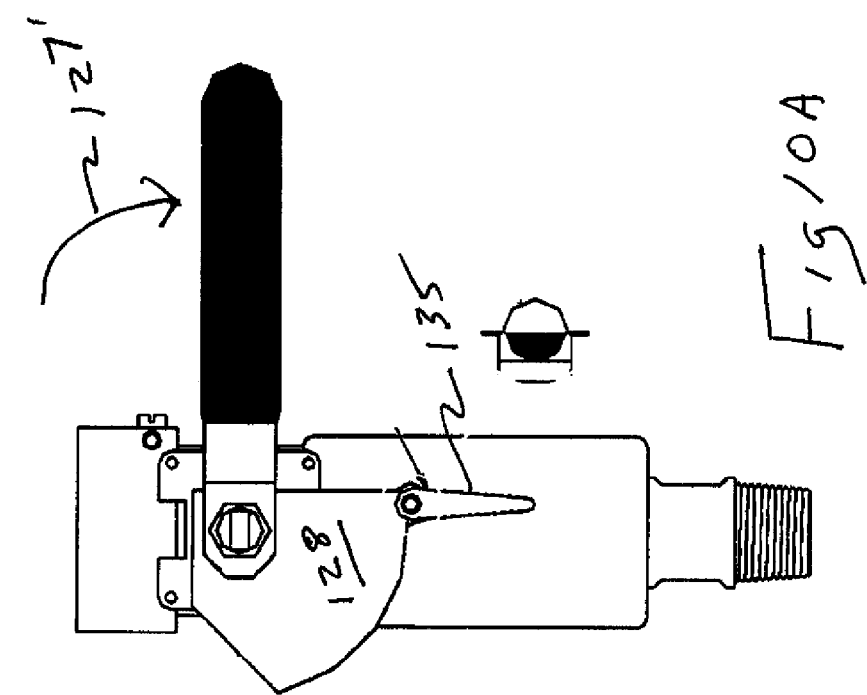
FIG. 10A is an opposite side view of the invention of FIG. 9A, illustrating the operation of the lock plate and showing the rack lock handle shown in a locked, inoperable position.
Figure 10C:
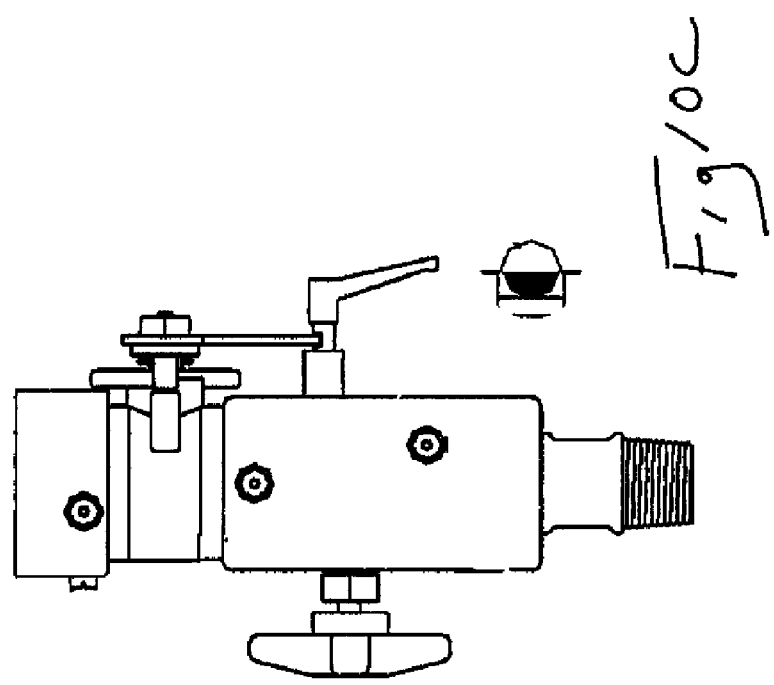
FIG. 10C is a front view of the invention of FIG. 10A, illustrating the lock plate associated with the hazop handle engaging the rack lock handle in a locked position, locking the rack in place, with the hazop valve controlled by the hazop handle in closed position.
Figure 10D:
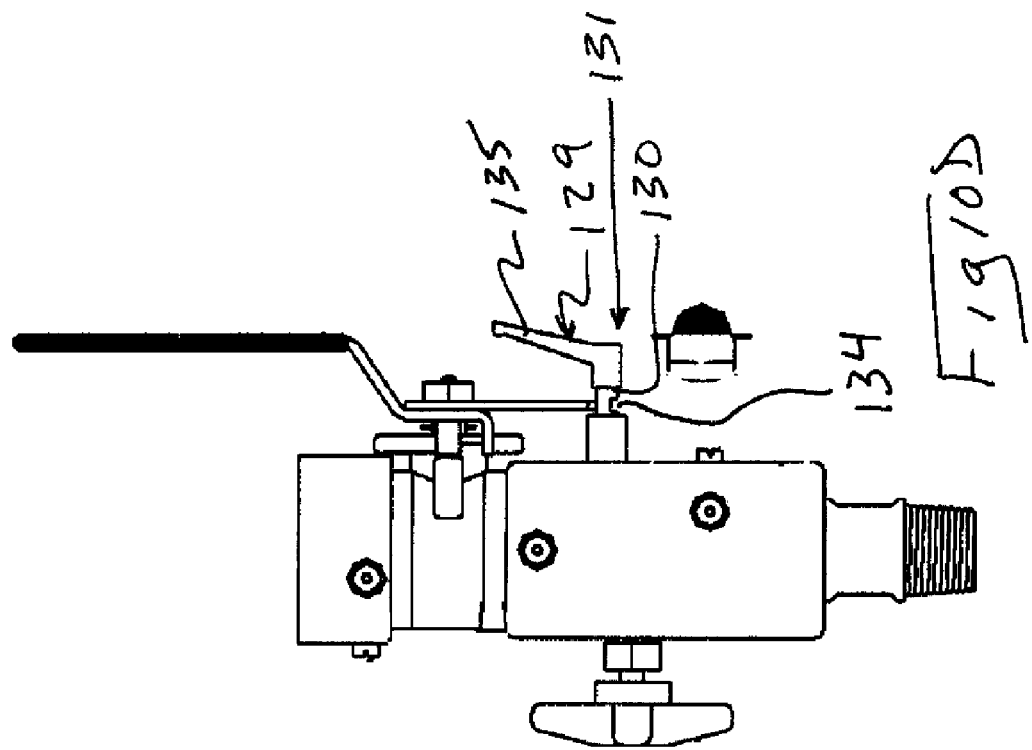
FIG. 10D is a front view of the invention of FIG. 10B, illustrating the lock plate associated with the hazop handle disengaged from the rack lock handle, allowing the rack lock handle to be rotated to the open position for raising or lowering of the probe. As shown, in this position, the hazop valve controlled by the hazop handle is in an open position.
Figure 13:
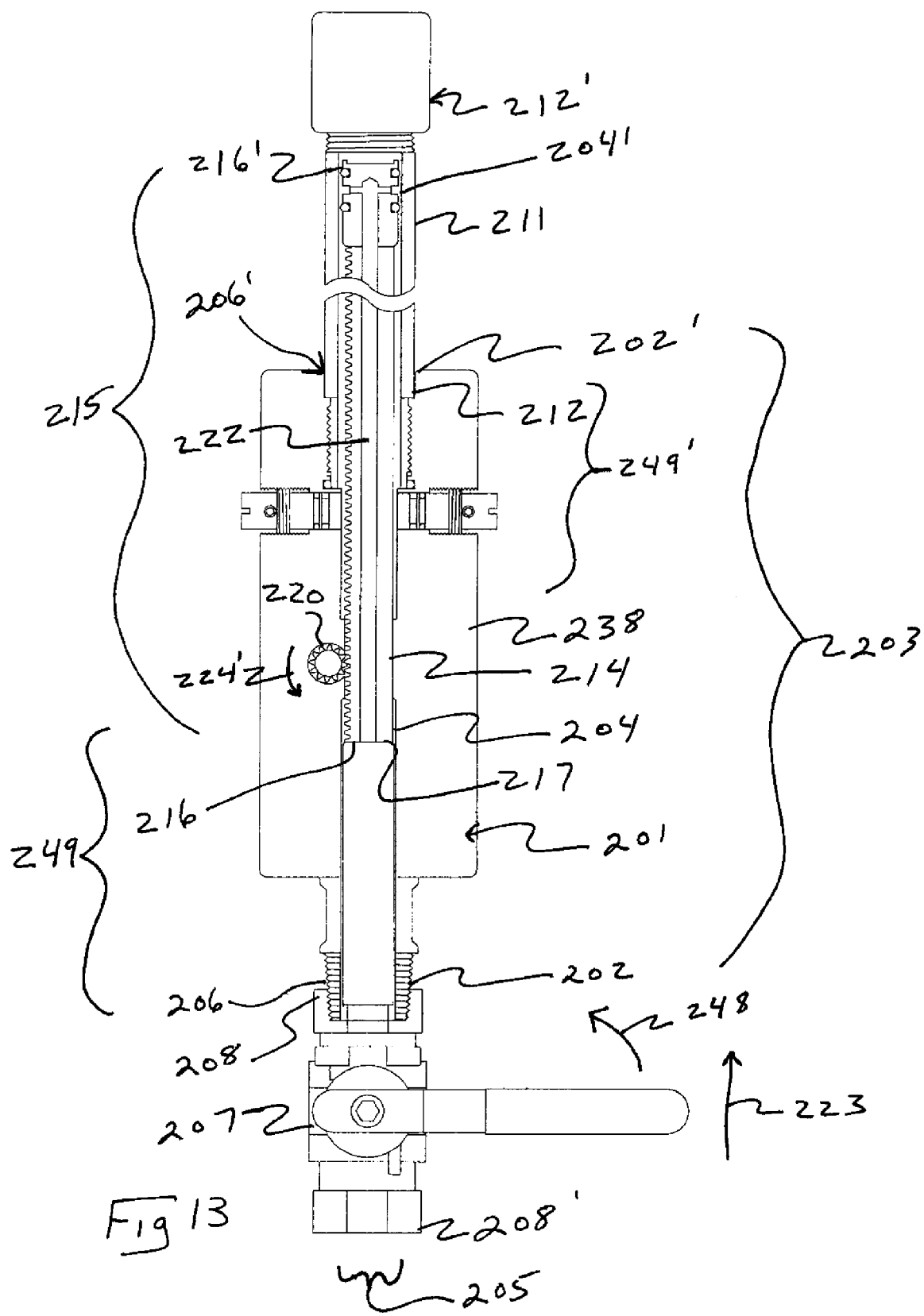
FIG. 13 is a side, rear, partially cut-away view of another embodiment of the invention suitable for insertion/retraction of the sample probe under high pressure, hazardous operation conditions (the Hazop probe), this embodiment without the Hazop valve of the embodiment of FIGS. 8-11, the sample probe being shown in the retracted position, non-sampling position, with the second end of the probe situated in the probe housing, as well as other features herein discussed, the hazop probe embodiment shown mounted to a process sample valve (shown in closed position) leading to a pressurized process stream.
Figure 13A:
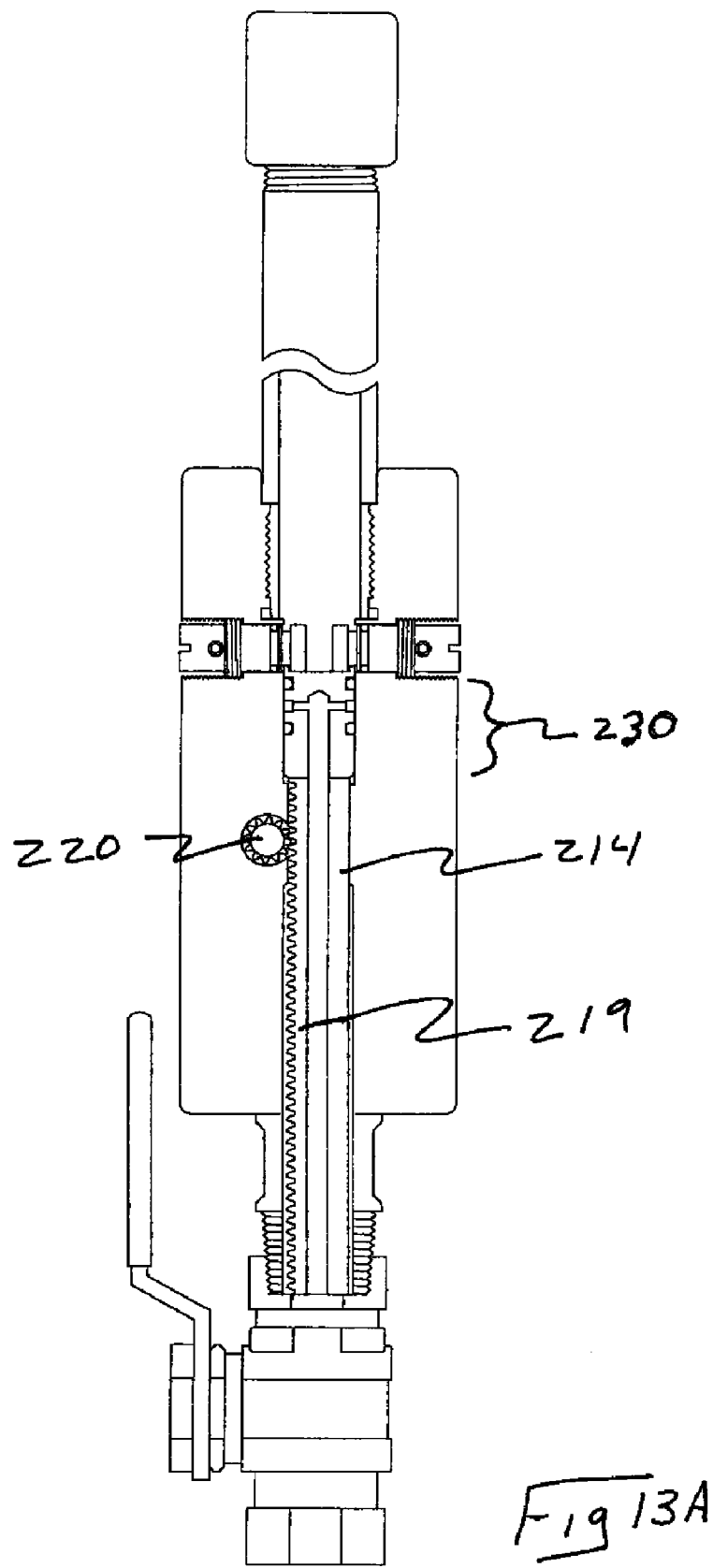
FIG. 13A is the rear view of the hazop probe assembly of FIG. 13, illustrating the process sample valve repositioned on its axis 90 degrees so that the handle does not block the view of the invention, the process sample valve opened with the first end of the sample probe passing through the open valve into the pressurized process stream, with the second end of the probe lowered into the probe body and locked in place via probe locks to a sampling position to direct sample to an outlet port.
Figure 13B:
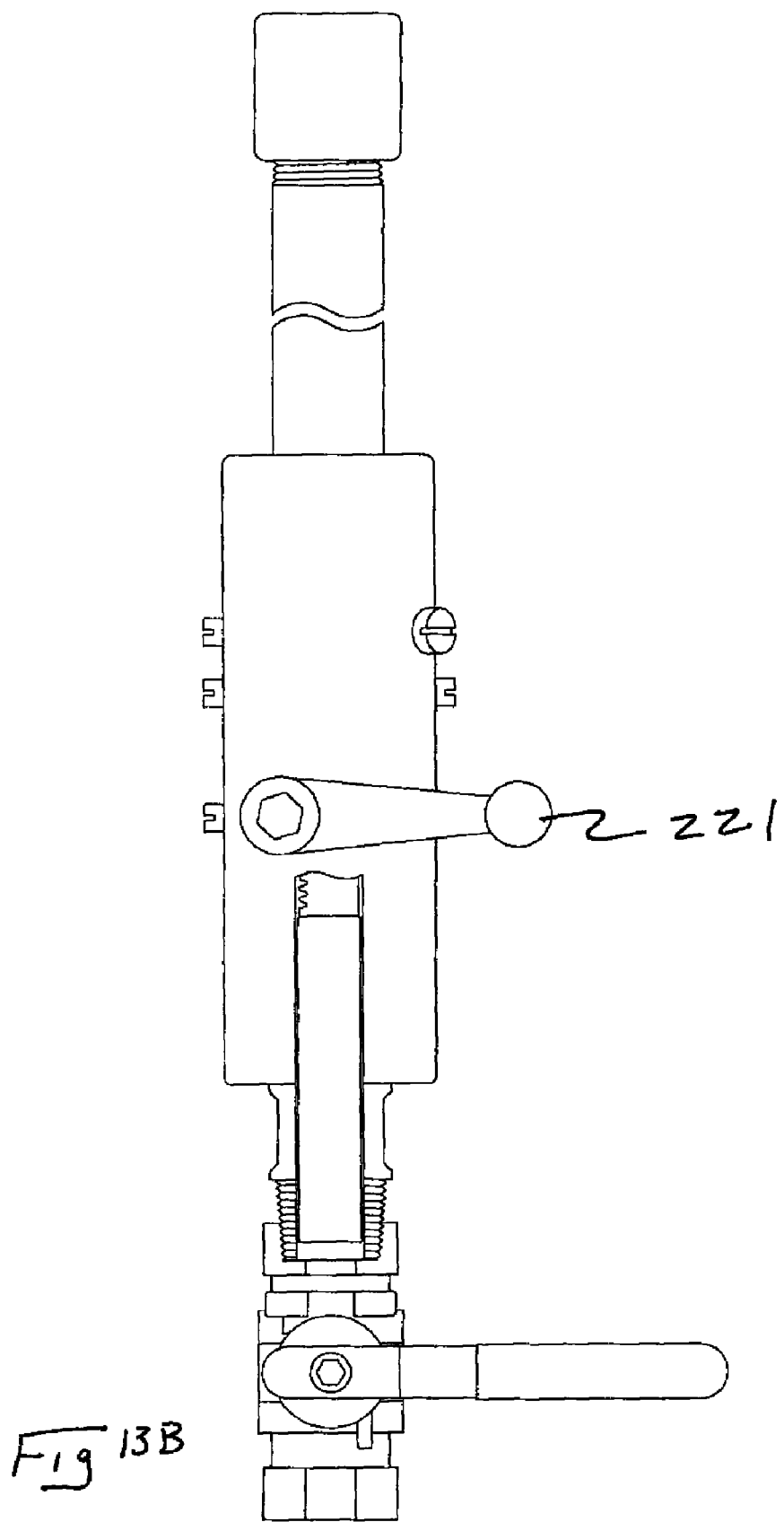
FIG. 13B is a front, partially cut-away view of the hazop probe assembly of FIG. 13, (but with the process sample valve again axially turned for illustration purposes) illustrating the pinion gear crank, the sample and vent passages and associated screw valves.

The second end 131' of the rod 130 is situated exterior the probe assembly 101 and has mounted thereto a rack lock handle 135 for selectively rotating rod 130 to engage 136 (lock), or disengage 136' (unlock) the lock pin from the locking groove (FIGS. 10B and 10D illustrate the rack lock handle 135 in the unlocked position in the current embodiment, while FIGS. 10A and 10C shows the rack lock handle 135 in the locked position).

Also situated exterior the probe assembly 101 on the rack lock apparatus 129 is a exterior locking groove 134 (shown formed on rod 130 adjacent to rock lock handle 135), the groove 134 formed so as to engage the outer edge 139 of lock plate 128, shown mounted to the hazop valve control handle 126 so as to lock the rack lock handle when the hazop valve control handle 126 is in the locked position via the outer edge of the lock plate engaging the exterior locking groove 134 (locking the probe in the out 123, deployed position), thereby interlinking the operation of the hazop valve 125, rack lock handle 135, and insertion/retraction of the probe via the crank knob or pinion gear handle 121.

Figure 9B:
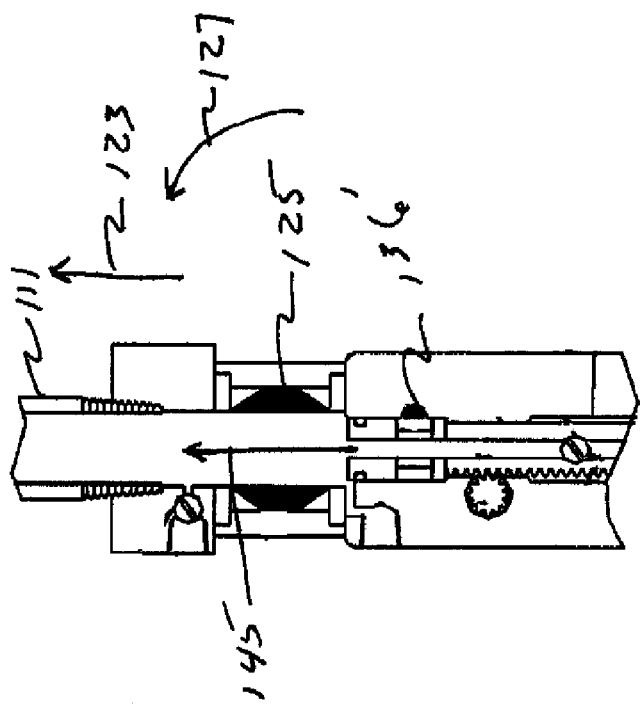
FIG. 9B is a side, cut-away view of the hazop probe of FIG. 9B, illustrating the hazop valve in an open position with the upper portion of the probe situated within the body, and the rack lock in an unlocked position.
Figure 9A:
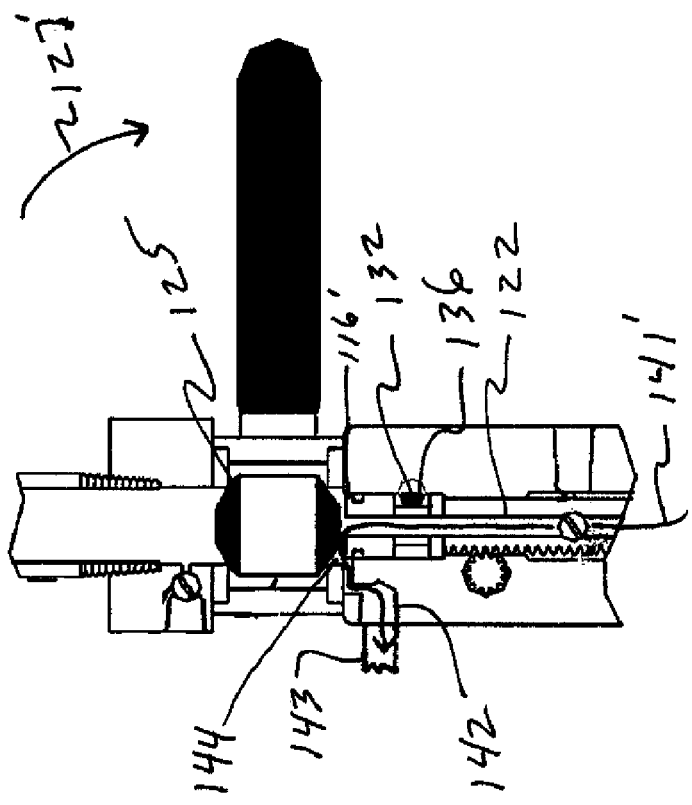
FIG. 9A is a side, cut-away view of the hazop probe of FIG. 8B, illustrating the hazop valve in a closed position with the upper portion of the probe situated within the body, and a rack lock incorporated in the present system, shown in a locked position.
Figure 9C:
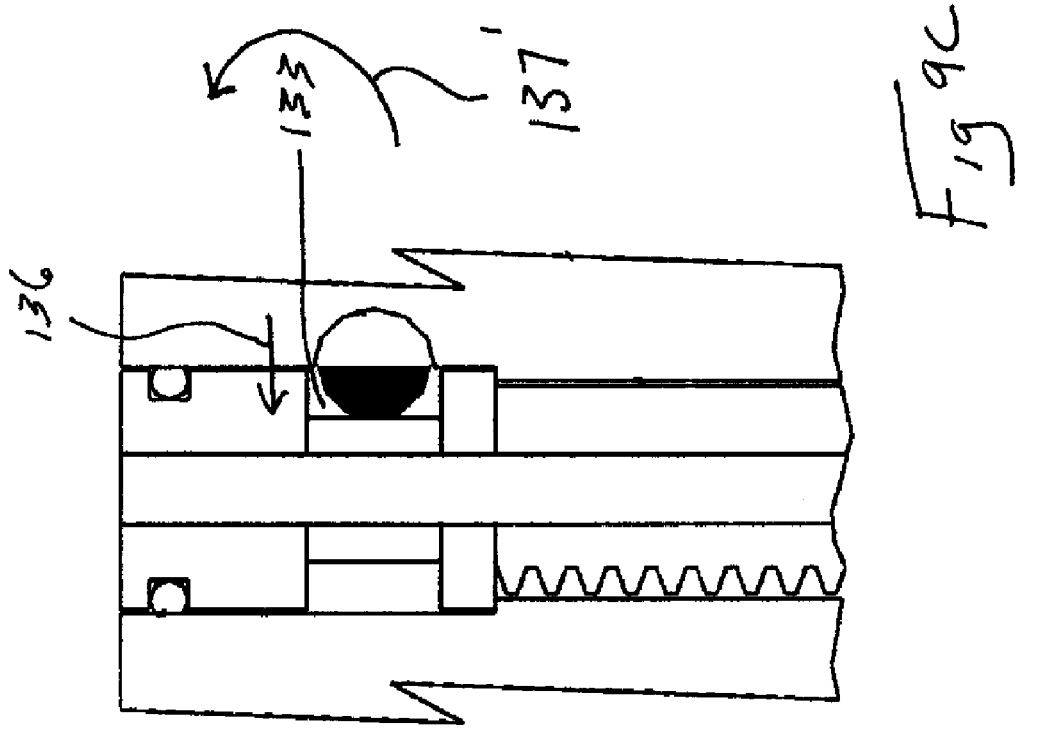
FIG. 9C is a side, cut-away, close-up view of FIG. 9A, illustrating the rack lock shown in a locked position.
Figure 9D:
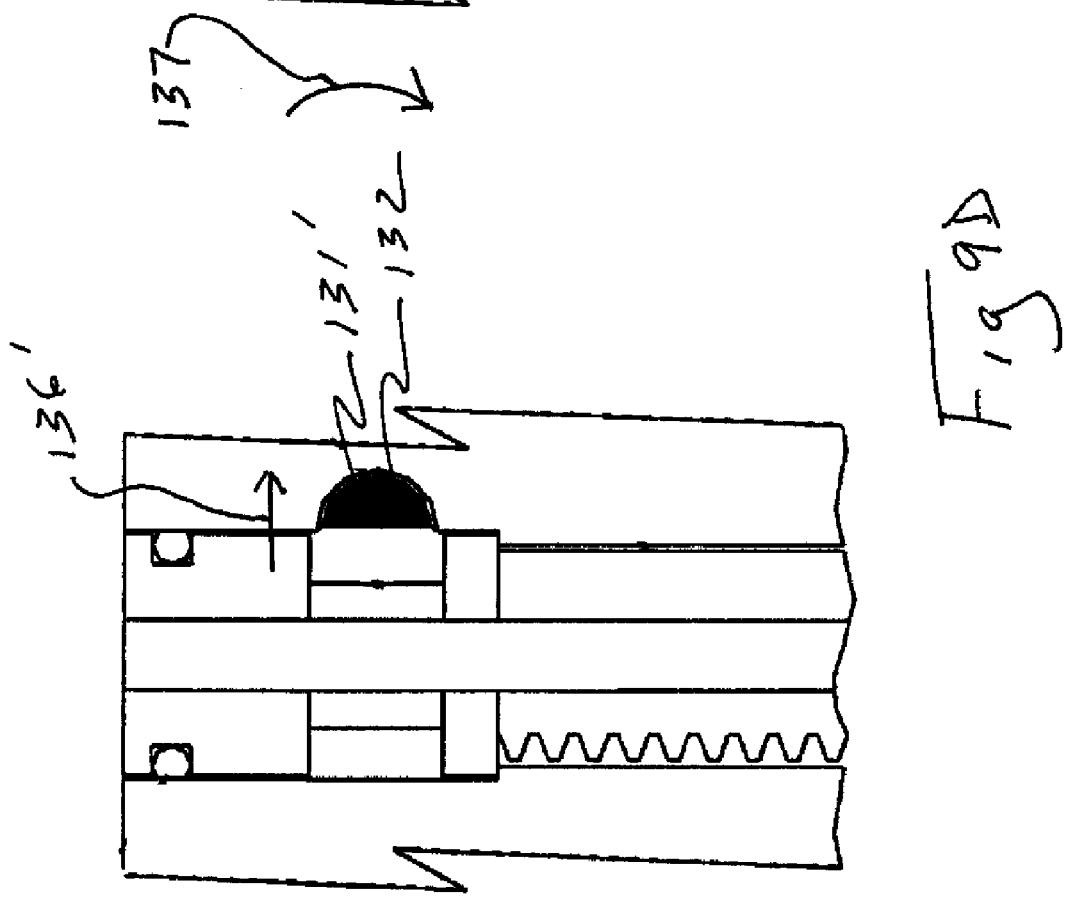
FIG. 9D is a side, cut-away, close-up view of FIG. 9B, illustrating the rack lock shown in an unlocked position.

Continuing with FIG. 9A and FIG. 11, with the hazop valve 125 is shown in the closed position 127', the lock pin 132 in the engaged position with the probe in the deployed position, sample gas 141, 141' may thereby pass through the length of probe conduit 122, entering at the probe tip 117 and exiting at the second end 116' of the probe, the gas thereafter passing through a clearance 144 formed between the top of the probe and the closed valve, then through sample passage 142 formed in the body of the probe, and out through sample tube 143. FIG. 9A illustrates the position of the second end 116' of the probe, retained in place via lock pin 132 in the engaged 136 position, such that there is a clearance or headspace between the second end 116' of the probe and the hazop valve 125, so as to allow passage of the sample gas 142 therebetween.

In use, the probe assembly is mounted to the closed valve 107 and sample 143 and vent tubes 147 are connected to the appropriate ports. The valve 107 may then be opened to allow pressure equalization in to the system, at which point the probe 114 (with appropriate probe tip apparatus thereon) may be lowered so that the probe tip situated in the pressurized fluid process for sampling, the lowering accomplished via cranking the pinion gear handle or crank knob 121. Once lowered in place, the rack lock handle 135 is turned to place the lock pin 132 into the engaged 136 position, locking the probe in place, as previously discussed. The hazop valve 125 can then be closed 127', at which point the lock plate 128 engages the exterior locking groove 134 associated with the rack lock apparatus 129, preventing un-locking of the probes position, and allowing sampling of the gas to occur as previously described.

Because the tubular housing 111 could be quite long (as discussed earlier), it may be desirable to remove said housing when the probe is sampling, which can occur over an extended period of time. With the Hazop valve closed, the tubular housing can be removed, and a plug 146 installed in its place, thereby significantly reducing the footprint of the system when in operation. Alternatively, the probe end can be sealed and locked, as opposed to simply closing the hazop valve.

Referring to FIG. 9B, when sampling is complete, with the tubular housing 111 in place, the hazop valve 125 is opened 127, allowing the sample gas 145 to pass into tubular housing, until the pressure has reached equilibrium, at which point the lock pin 132 is rotated via rack lock handle 135 until it is in the disengaged 136' position, allowing the probe to be raised, via cranking of the pinion gear to raise the probe via the rack 119, until the probe tip is positioned in 123' the probe assembly, and the second end 116' of the probe situated in the tubular housing.

With the probe in the fully retracted position (shown in FIG. 8D), with the second end 116' of the probe enclosed via tubular housing 111 and the probe tip and any apparatus thereon at the first end 116 enclosed in the probe assembly conduit 104. At this point, the valve 107 can be closed and the probe assembly removed (after venting of any pressurized gas in the probe assembly), if desired.

FIGS. 13-17 contemplate a more simplified embodiment of the invention of FIGS. 8-12, which embodiment does not require an expensive hazop valve, nor is there required the rack lock as taught in the previous embodiment.

Hazop Embodiment Without Hazop Valve

Referring to FIGS. 13-13B, 14A-14B, 15, and 17 a second hazop probe embodiment of the present invention is provided which does not require a hazop valve; this can be desirable as a high pressure valve can be quite costly. Even without a valve, however, the unique design employed in this second hazop probe embodiment effectively employs a balanced pressure technique in its operation, wherein the pressure is equalized in the housing to that of the pressurized process, so as to avoid the need for packing glands or the like.

As shown, the probe assembly 201 is provided having first 202 and second 202' ends (with a body 238 therebetween) and a length 203, the probe assembly having a conduit 204 formed through the length thereof having an interior diameter 205 (which varies as further explained herein), and threaded connections 206, 206' at each opposing end 202, 202'.

Figure 17:
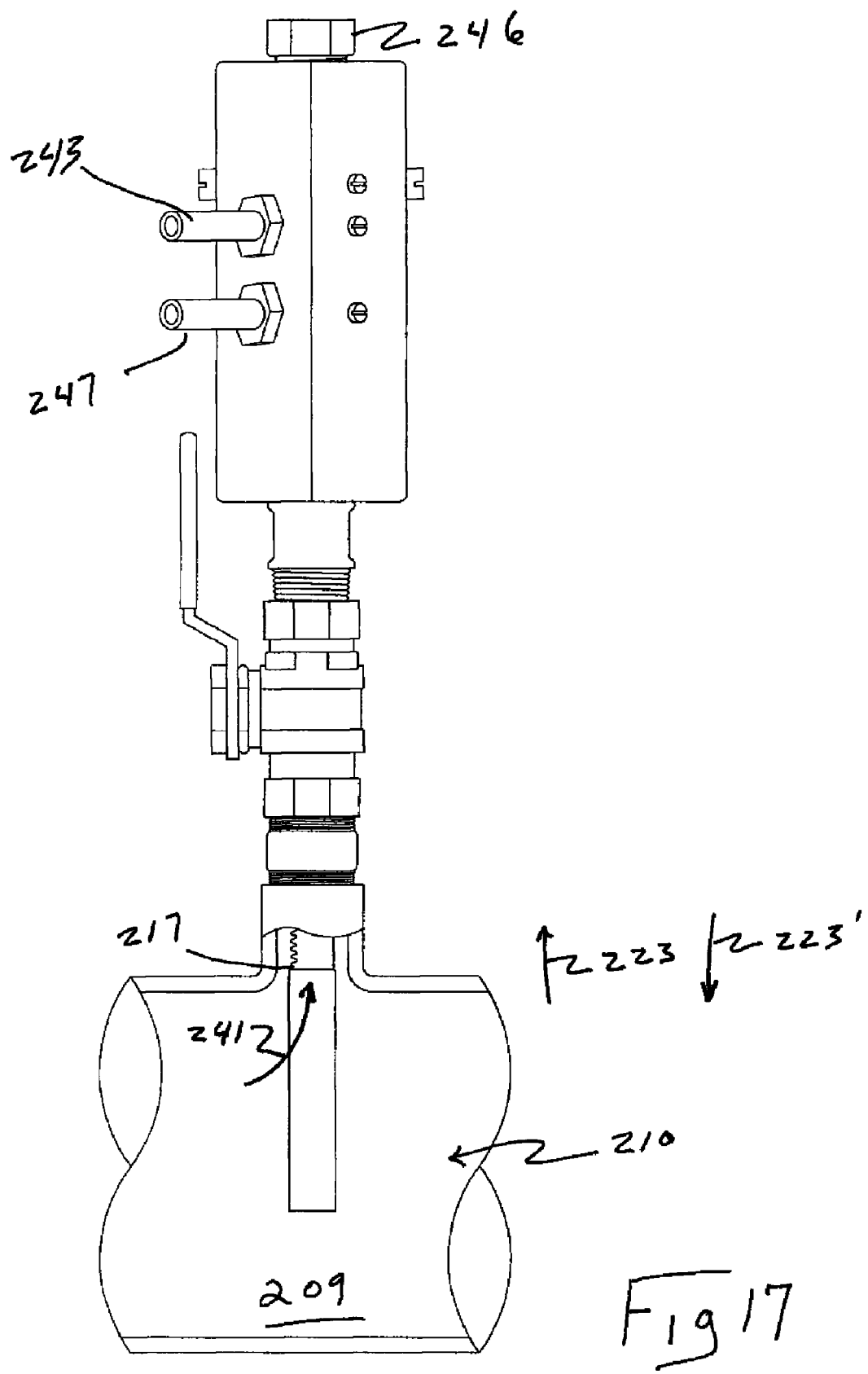

First end 202 of the probe assembly is formed to engage, via threaded connection 206 (for example, via ¾" N.P.T.), the first end 208 of a valve 207 or the like, the second end 208' of the ball valve threadingly engaging passage to a pipe or vessel 209 containing a pressurized fluid process 210 (FIG. 17).

A tubular housing 211 is provided having first 212 and second 212' ends, the first end 212 preferably being threaded to engage said threaded connection 206' at said second end 202' of said probe assembly. The tubular housing has a conduit 204' formed along its length and, when connected to the probe assembly, provides an enclosure effectively extending the conduit 204 formed through the probe assembly 201.

Conduits 204, 204' are formed in the probe assembly and tubular housing to enclose a sample probe 214 having first 216 and second 216' ends and a length 215, the first end 216 of the sample probe forming the probe tip 217 which is shown threaded 213' to engage a sample tip, which can include a phase separation membrane, etc, as discussed in the previous embodiments supra, and which sample tip which comprises the end immersed into the pressurized fluid process during sampling. While the use of a sample tip is illustrated, it is not required for the operation of the system, i.e., the sample probe may be used without a sample tip.

Continuing with FIGS. 13, 13A, 13B and 15, a linear gear rack 219 is formed along at least a portion of the length 215 of the sample probe for longitudinally adjusting the position of the sample probe 214 throughout conduits 204, 204', the rack formed to engage a rotatable pinion gear 220, a portion of which is situated in conduit 204, which pinion gear is driven by a pinion gear handle 221 or crank knob, located exterior the probe assembly, and mounted at the body 238 of the probe assembly.

The rack 219 and pinion 220 combination is formed to longitudinally position the probe tip 217 into 223 the lower portion 249 of conduit 204, in a retracted position (shown in FIG. 13), or out of 223' the conduit 204, in a deployed position (Shown in FIG. 17), into a pressurized process stream, via rotation 224', 224 of the pinion gear 220 via pinion gear handle 221, respectively.

Continuing with FIGS. 13-13A, 14A-14B, and 15, in lieu of the hazop valve taught in the previous embodiment of the invention, the present invention utilizes a lock system comprising first and second probe locks 225, 225', coupled with a system for providing a sealed sampling interface, for use during the sampling operation, as will be described below.

The upper, second end 216' portion of the sample probe 214 has a slightly larger outer diameter than the rest of the probe so as to form a sampling interface 230 portion, the sampling interface having situated thereabout first 218 and second 218' 0-rings which are formed to slidingly engage the inner diameter 205 forming the walls of conduit 204 in an area above the pinion 220 in fluidly sealed manner.

The probe has a conduit 222 running almost its entire length, from the probe tip 217 to the vicinity of the second end 216' (which is closed). A lateral sampling passage 226 is provided between the O-rings 218, 218' near the second end of the probe to selectively interface an adjacent sample passage 226' formed in the probe assembly.

As shown, the probe assembly conduit 204 may be divided into a lower portion 249 and an upper portion 249', with the upper portion (shown above the pinion) having an inner diameter formed such that the inner walls of said passage slidingly engage the o-rings 218, 218' on the probe to provide a fluid tight seal, as discussed, with the lower portion 249 (below the pinion 220) having a larger inner diameter to accommodate the probe tip 217 and any apparatus affixed thereto.

Between the upper 249' and lower 249 portions of the conduit is an intermediate portion 249", which, in the present embodiment, has a lesser internal diameter so that the outer diameter of the sampling interface 230 portion of the sample probe cannot pass therethrough, and upon lowering the sample probe through the conduit 204 (via the rack/pinion system) said sampling interface "bottoms out" at point 257 and is unable be further lowered at the intermediate portion 249". At this position, the lateral sample passage 226 of the sample probe and the assembly sample passage 226 are in general alignment or at least communication (the sampling mode), with the probe locks 225, 225' positioned above the sampling interface 230 so as to selectively lock the sampling interface in the sampling mode.

Figures 14A, 14B:
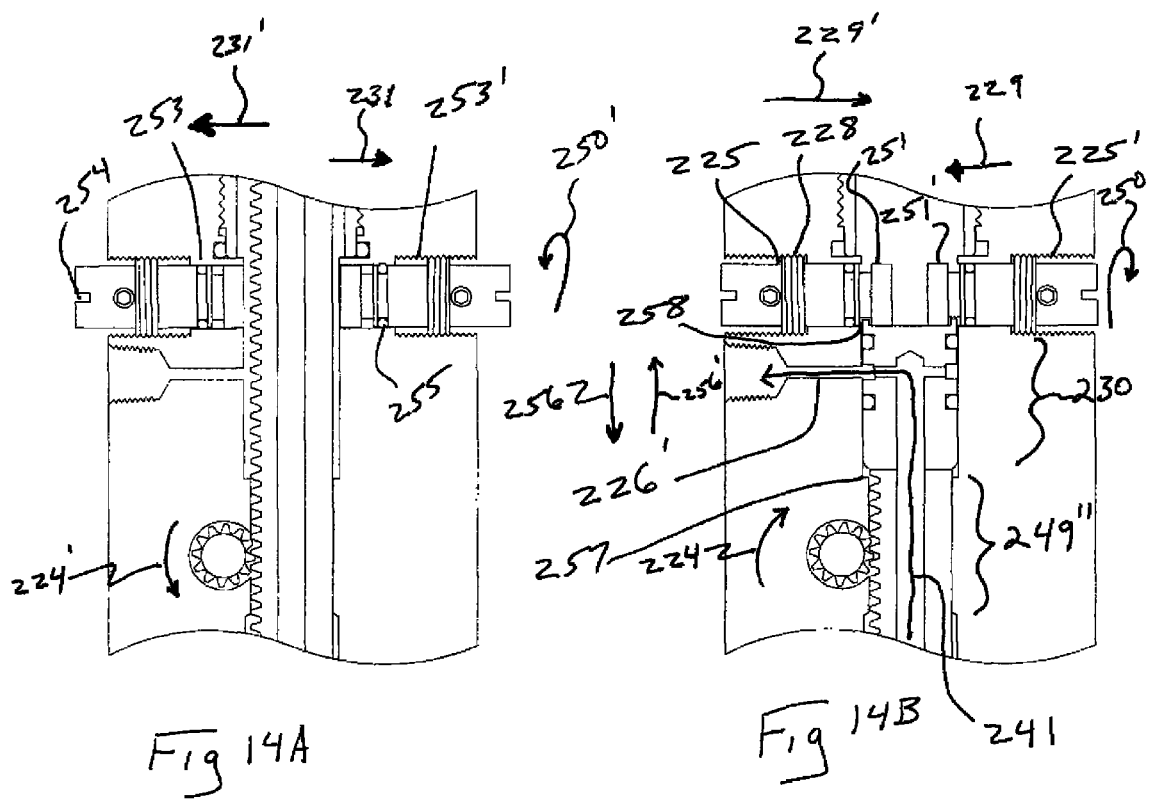
FIG. 14A is a rear close-up, partially cut-away, side view of the invention of FIG. 13 illustrating first and second probe locks in an open position, with the sample probe in the retracted position.
FIG. 14B is a rear close, up, partially cut-away, side view of the invention of FIG. 13 illustrating the first and second probe locks in a closed position, the sample probe lowered to is extended position, with the second end of the probe situated below the probe locks, locking the probe into position and the isolation seals at the second end of the probe sealing the flow of sample gas to direct same to the sample passage.
Figure 15:
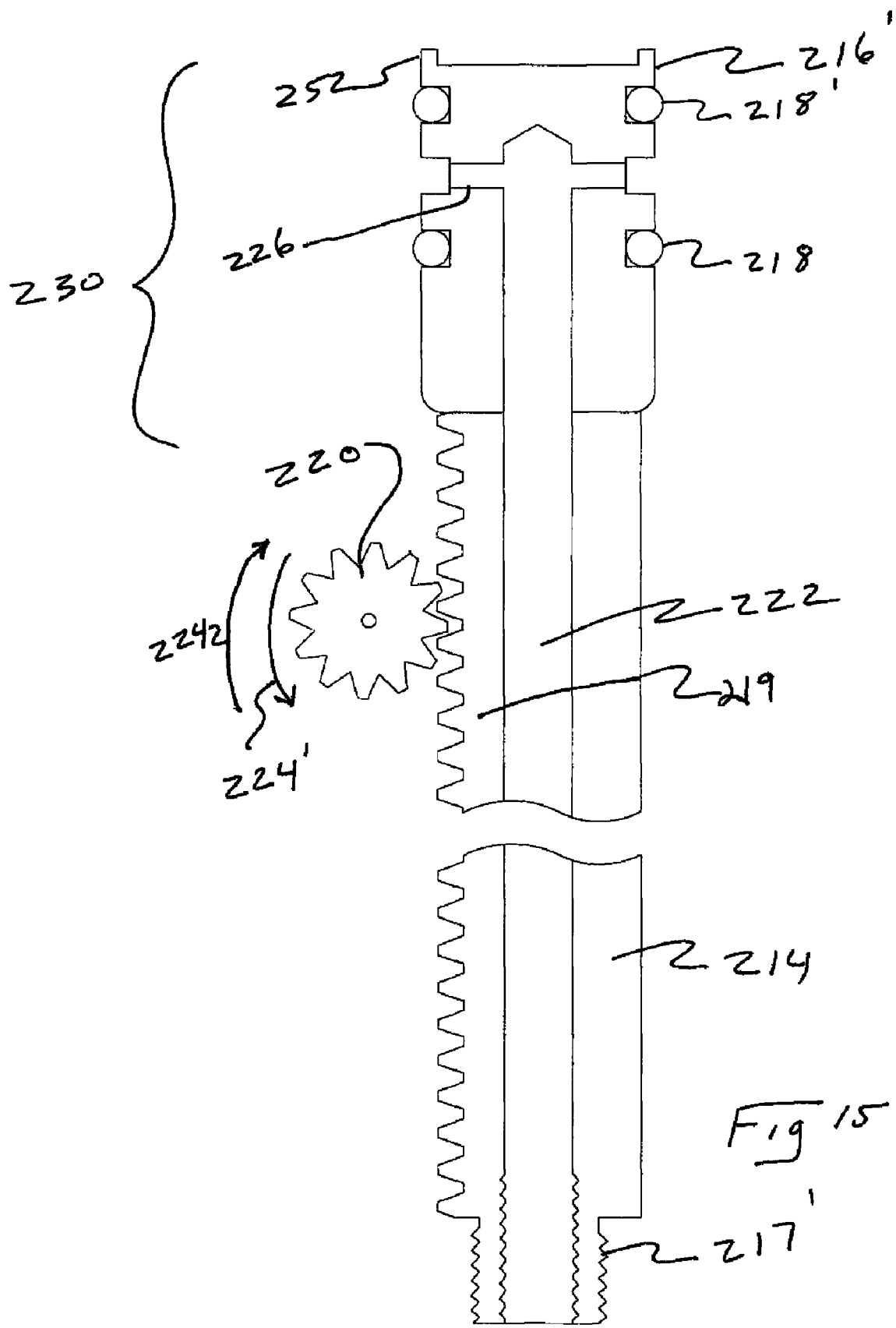
FIG. 15 is a side view of the invention of FIG. 13 illustrating the sample probe and the associated rack and pinion drive for raising and lowering said probe.
Figure 16:
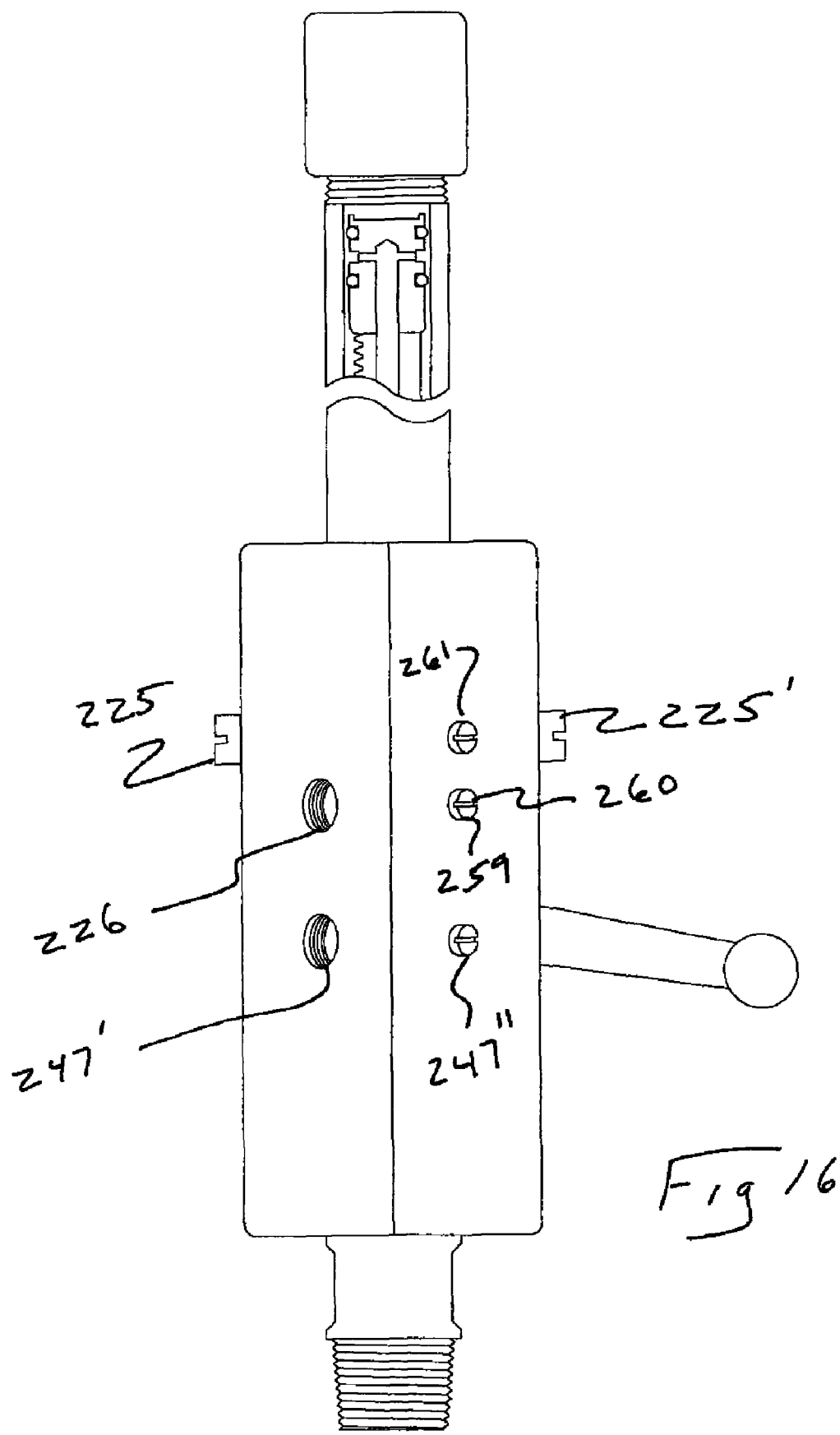
FIG. 16 is a side, isometric, partially cut-away view of the invention of FIG. 13 illustrating the probe body, the tubular housing, and positioning of the sample passage and vent passage, the screw valves, and the probe locks.

With the sampling interface positioned in the sampling mode, the first and second probe locks may be implemented by threadingly 228 engaging the lateral threaded apertures formed in the probe assembly, to selectively extend 229 said locks into the probe assembly conduit (as shown in FIG. 14B), selectively locking the probe in the extended 223' position.

Each of the probe locks has first and second ends, and a length which is threaded for interfacing with a threaded lateral passage formed in the probe assembly, which threaded lateral passage leads to the probe assembly conduit. The first end of the probe lock includes an interface (shown is a flathead screwdriver slot), although other interfaces may include Allen wrench socket, Phillips, or the like.

The opposing, second end of the probe lock is formed to selectively enter and partially block the probe assembly conduit for locking the probe in place. The second end thereby may include a flange or the like, as will be disclosed below. Each probe lock may also include an o-ring 255 O-ring or the like as a pressure seal to prevent leakage of pressure from the probe assembly conduit to the outside.

The actuating of the probe locks 225, 225' is accomplished by rotating each of said locks via, for example, a screw driver or other tool (depending upon the interface provided) at their respective slot or other interface provided exterior the probe assembly (FIG. 14A illustrates a slot 254 for a flat head screwdriver).

As indicated, each probe lock 225, 225' may have a flange 251, 251' respectively, formed to engage a raised rim 252 situated at the second end 216' of the sample probe, which can be used to lock the system in sampling mode, by slightly lowering 256 (via turning 224 pinion 220) the probe until the lower portion of the sampling interface 230 reaches the bottom out point 257, then extending 229 the probe locks, then slightly raising 256' the probe (via turning 224' the pinion 220) to lift the probe until the raised rim 252 engages the area 258 between the flanges 251, 251' and the wall forming the conduit 204 inner diameter 205. The probe locks may then be rotated 250' to slightly retract same, so that the flanges engage the raised rim 252, locking the probe locks, as well as the sample conduit, in the sampling mode.

It is important that the sample probe have a length such that, when the probe tip is lowered into the pressurized fluid process 210 for sampling, the sample interface 230 at the second end of the probe be positioned in the sampling mode, above, and when the probe tip is retracted into the probe assembly, the sample interface 230 is positioned in the tubular housing.

To this end, it is noted that the tubular housing 211 can vary significantly in length to accommodate most probe lengths, which can vary depending upon the installation and application. More specifically, in some applications, it may be advantageous to utilize an intermediary pipe between the second end 208' of the valve 207 and the threaded connection for pipe or vessel 209 containing pressurized fluid process 210.

Such may be the case, for example, where the pipe or vessel 209 is situated below ground several feet, in which case an intermediary pipe running from the pipe or vessel 209 to ground level, which then engages the valve 207, can be provided to facilitate accessibility to the system. In such an application, the probe would have to have a length to accommodate the intermediary pipe, and the tubular housing 211 would likewise have to have a length adequate to accommodate the extended probe length. Thus, the probe length can vary significantly depending upon application.

It is also noted that, although the present embodiment illustrates the probe assembly and the tubular housing 211 as being separate components, it should be understood that this is an example of a design of the present invention and that the tubular housing and probe assembly, when engaged, can work as a single housing for the probe. Thus, the present example is not intended to be limiting as to the structure of the housing, and the present invention may accordingly practiced with a single housing having the entire length of the probe conduits 204, 204' therein.

Continuing with FIGS. 13, 13A, 15 and 17, in the extended, sampling position, with the probe tip lowered into the pressurized process (as shown in FIG. 17), via the rack and pinion system, and locking the probe in place as described above, the sample gas 241 may thereby pass through the length of probe conduit 222, entering at the probe tip 217 and exiting via the lateral sampling passage 226 at the second end 216' of the probe, then through sample passage 226' formed in the probe assembly 201.

Gauge port passage 247' comprises a lateral passage to probe conduit 204 for interfacing an exteriorly mounted gauge, which passage may be opened or closed via screw valve 247", while screw valve 259 can be used to selectively open or close sample passage 242.

In use, the probe assembly 201 is mounted to the closed valve 207 and sample 243 and gauge tubes 247 are connected to the appropriate ports. The valve 207 may then be opened 248 to allow pressure equalization in to the system, wherein the pressurized fluid process passes through probe assembly conduit 204 and tubular housing 211 conduit 204' increase until the pressure is equal to that of the pressurized fluid process.

Probe 214 (with appropriate probe tip apparatus thereon) may be lowered through the open valve 107 via rotating 224 pinion 220 until the probe tip 217 situated in the pressurized fluid process for sampling, the lowering accomplished via cranking the pinion gear handle or crank knob 221 until the sampling interface 230 can no longer be lowered due to it the bottom out point 257 at intermediate portion 249".

Once lowered in place, the probe locks 225, 225' are extended 229, 229' into conduit 222, locking the probe rack into position such that lateral sampling passage 226 communicates with sampling passage 226' in probe assembly, with o-rings 218, 218 containing the system. With screw valve 259 opened (via turning the screw head 260 as shown exterior the system), the sample fluid flows to sample tube for sampling, storage or other use.

Upon completion of sampling, screw valve 259 is closed, closing off flow of the sample passage 257 formed in the probe assembly. A bypass (not shown, running between the probe assembly conduit 204 and tubular housing conduit 204', may be opened via a valve or the like to equalize the pressure between same. The probe locks 225, 225' are then retracted 231, 231' by rotating same 250, 250'; the probe may be slightly lowered or extended 256 if required by rotating 224 pinion 220 if required for clearance, until the probe locks clear the conduit 204, then the pinion can be rotated 224' via handle 221 until the probe tip is situated in the conduit 204, at which point valve 207 can be closed. The housing/probe assembly may be depressurized via opening screw valve 261, which vents the conduit 222 via a vent passage. At this point, the probe assembly (or tubular housing, as discussed below) can be removed, if desired.

Because the tubular housing 211 could be quite long (as discussed earlier), it may be desirable to remove said housing when the probe is sampling, which can occur over an extended period of time. With the probe locked in the sampling position, the tubular housing can be removed, and a plug 246 installed in its place, thereby significantly reducing the footprint of the system when in operation. A vent associated with the tubular housing conduit may be provided to selectively open, via valve or the like, to equalize the tubular housing with the atmospheric pressure prior to removal. Upon re-installation of the tubular housing conduit to a pressurized system, a bypass (discussed above) between the probe assembly conduit 204 and the tubular housing conduit 204' may be utilized to equalize the pressure between same.

| Recitation of the Elements of the Invention | |
|---|---|
| 1. | Probe assembly |
| 2. | Housing assembly |
| 3. | First end of housing assembly |
| 4. | Second end of housing assembly |
| 5. | Male N.P.T. threads |
| 6. | Threaded outlet port |
| 7. | Conduit |
| 8. | First end of conduit |
| 9. | Second end of conduit |
| 10. | First end of probe |
| 11. | Second end of probe |
| 12. | Sliding seal |
| 13. | Pinion gear |
| 14. | Rack gear |
| 15. | Pressurized fluid process |
| 16. | Pipe or vessel |
| 17. | Fully opening valve |
| 18. | Nipple |
| 19. | Opening in wall of pipe or vessel |
| 20. | Pinion gear handle |
| 21. | Pinion gear shaft |
| 22. | Valve handle |
| 23. | Fluid communication passage |

-continued

Recitation of the Elements of the Invention

| | | |
|---|---|---|
| 24. | Cavity A | |
| 25. | Passage A | |
| 26. | Passage B | |
| 27. | Annulus | |
| 28. | Threaded opening to passage A | |
| 29. | Phase separating membrane/filter assembly | |
| 30. | Probe | |
| 31. | Sensor | |
| 32. | Sensor cable | |
| 33. | Attachment plate for corrosion coupon | |
| 34. | Closed end cap | |
| 35. | Closed end cap well | |
| 36. | Temperature sensor | |
| 37. | Flexible conduit | |
| 38. | First end of temperature sensor | |
| 39. | Second end of temperature sensor | |
| 40. | Finned outer surface | |
| 41. | Probe travel locking screw | |
| 42. | Threaded opening | |
| 43. | Inner wall of housing assembly | |
| 44. | First end of probe travel locking screw | |
| 45. | First end of nipple | |
| 46. | Second end of nipple | |
| 47. | Second end of conduit | |
| 48. | Temperature sensor cable | |
| 49. | Inner wall of second end of housing assembly | |
| 50. | Seal | |
| 51. | Flows | |
| 52. | | |
| 53. | Rotating | |
| 54. | Rotating | |
| 55. | Extended | |
| 56. | Rotating | |
| 57. | Rotating | |
| 58. | Unscrewed | |

HAZOP PROBE EMBODIMENT (with Hazop Valve)

| | |
|---|---|
| 101 | probe assembly |
| 102,' | first, second ends |
| 103 | length |
| 104,' | probe assembly conduit |
| 105 | ID |
| 106,' | threaded connections at opposing ends |
| 107 | valve |
| 108,' | first, second ends |
| 109 | vessel |
| 110 | pressurized fluid process |
| 111 | tubular housing |
| 112,' | first, second ends |
| 113 | threaded |
| 114 | probe |
| 115 | length |
| 116 | first, second ends |
| 117 | probe tip |
| 118 | o-ring seal |
| 119 | linear rack |
| 120 | pinion gear |
| 121 | pinion gear handle/crank knob |
| 122 | probe conduit |
| 123,' | probe out, in |
| 124.' | pinion rotation |
| 125 | hazop valve |
| 126 | hazop valve control handle |
| 127,' | open, close valve |
| 128 | lock plate |
| 129 | rack lock apparatus |
| 130 | rod |
| 131,' | first, second ends |
| 132 | lock pin |
| 133 | interior locking groove |
| 134 | exterior locking groove |

HAZOP PROBE EMBODIMENT (with Hazop Valve)

| | |
|---|---|
| 135 | rack lock handle |
| 136,' | engage, disengage |
| 137,' | rotation |
| 138 | body |
| 139 | outer edge of lock plate |
| 140 | lock |
| 141 | sample gas |
| 142 | sample passage |
| 143 | sample tube |
| 144 | clearance |
| 145 | sample gas |
| 146 | plug |
| 147,' | vent tubes |
| 148,' | valve (107) open, closed |
| 149,' | lower, upper portions of conduit |
| 150 | |

HAZOP PROBE EMBODIMENT (without Hazop Valve)

| | |
|---|---|
| 201 | probe assembly |
| 202,' | first, second ends |
| 203 | length |
| 204,' | probe assembly conduit |
| 205 | ID |
| 206,' | threaded connections at opposing ends |
| 207 | valve |
| 208,' | first, second ends |
| 209 | vessel |
| 210 | pressurized fluid process |
| 211 | tubular housing |
| 212,' | first, second ends |
| 213 | threaded |
| 214 | probe |
| 215 | length |
| 216 | first, second ends |
| 217 | probe tip |
| 218 | o-ring seal |
| 219 | linear rack |
| 220 | pinion gear |
| 221 | pinion gear handle/crank knob |
| 222 | probe conduit |
| 223,' | probe out, in |
| 224.' | pinion rotation |
| 225,' | probe locks |
| 226,' | lateral sampling passage, probe assembly sampling package |
| 227,' | |
| 228 | threadingly |
| 229, | extend |
| 230 | sampling interface |
| 231,' | retract |
| 232 | turning |
| 233 | |
| 234 | |
| 235 | |
| 236,' | |
| 237,' | rotation |
| 238 | body |
| 239 | outer edge of lock plate |
| 240 | lock |
| 241 | sample gas |
| 242 | sample passage |
| 243 | sample tube |
| 244 | clearance |
| 245 | sample gas |
| 246 | plug |
| 247,','' | gauge tube, valve |
| 248,' | valve (207) open, closed |
| 249,' | lower, upper portions of conduit |
| 250 | rotating |
| 251,' | flange |
| 252 | raised rim |
| 253 | lateral apertures |

-continued

| HAZOP PROBE EMBODIMENT (without Hazop Valve) | |
| --- | --- |
| 254 | slot |
| 255 | O-ring/isolation seal |
| 256,' | lowering, raising |
| 257 | bottom out |
| 258 | area |
| 259 | sample passage screw valve |
| 260 | screw head |
| 261 | housing vent |

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A probe housing assembly for insertion and retraction of a probe into a pressurized vessel, comprising:
    a probe having first and second ends and a length, said probe having an internal fluid passage formed therethrough extending from said first end of said probe to said second end of said probe;
    a housing having first and second ends, said housing having an internal cavity formed therethrough extending from said first end of said housing to said second end of said housing, said housing formed to engage, in a fluidly sealed manner, a pressurized fluid process in said pressurized vessel;
    said probe slidingly disposed in said internal cavity formed in said housing in an approximate coaxial relationship with said housing;
    said probe engaging said housing so as to provide selective extension of said first end of said probe through and beyond said first end of said housing, so as to contact said pressurized fluid process in said pressurized vessel;
    wherein said length of said probe is situated within said internal cavity formed in said housing upon retraction of said probe into said housing such that, upon said pressurized fluid process entering said housing, a pressure equalization is provided within said housing and said pressurized vessel, so as to eliminate pressure differential between said pressure vessel, said housing and said probe.

2. The probe housing assembly of claim 1, wherein an outlet port is formed in the vicinity of said second end of said housing, said outlet port formed to allow fluid communication with the internal fluid passage of said probe.

3. The probe housing assembly of claim 2, wherein said outlet port is threaded for mechanical attachment and fluid communication with an external device.

4. The probe housing assembly of claim 1, wherein a sliding fluid seal is formed between said probe and said internal cavity formed in said housing.

5. The probe housing assembly of claim 1, wherein said first end of said housing engages said pressurized vessel via a threaded attachment.

6. The probe housing assembly of claim 1, wherein there is further provided a valve associated with said housing formed to selectively open and close said internal cavity formed in said housing.

7. The probe housing assembly of claim 6, wherein there is provided an outlet port formed in said housing to allow fluid communication with the internal fluid passage of said probe when said probe is in communication with a pressurized fluid process.

8. The probe housing assembly of claim 7, wherein there is provided a probe locking mechanism to lock said probe in position.

9. The probe housing assembly of claim 8, wherein said valve includes a locking interface to lock said probe locking mechanism.

10. The probe housing assembly of claim 6, wherein said valve is configured so as to lock a rack lock when said valve is in a closed position.

11. The probe housing assembly of claim 10, wherein there is provided on said valve a lock plate formed to lock said rack lock.

12. The probe housing assembly of claim 1, wherein there is further provided a locking mechanism for locking said first end of said probe in a fixed position.

13. The probe housing assembly of claim 1, wherein said housing and probe engage one another via rack and pinion formed to facilitate the selective extension and retraction of said probe from said housing.

14. The probe housing assembly of claim 1, wherein said housing and said probe engage one another via a friction drive arrangement formed to facilitate the selective extension and retraction of said probe from said housing.

15. The probe housing assembly of claim 1, wherein said first end of said probe has a threaded opening.

16. The probe housing assembly of claim 1, wherein there is further provided a phase separating membrane/filter assembly engaging said first end of said probe, said phase separating membrane/filter assembly formed to reject liquid and solid particles, while allowing the passage of gas or vapors into said passage formed in said probe.

17. The probe housing assembly of claim 1, wherein there is further provided a sensor engaging said first end of said probe, said sensor having a communication cable extending through said passage formed in said probe.

18. The probe assembly of claim 1, wherein there is further provided a corrosion coupon engaging said first end of said probe for selective insertion into said pressurized fluid process via said probe.

19. The probe assembly of claim 1, wherein there is further provided a closed end cap engaging said first end of said probe, said closed end cap having a cavity formed therein, said end cap communicating with said passage formed in said probe to provide a well;
    whereby a sensor can be lowered into said well extending from said probe, and said probe lowered into said pressurized fluid process, such that said well remains at atmospheric pressure, said probe engaging said pressurized vessel to seal said well from said pressurized fluid process, allowing said sensor to analyze said pressurized fluid process while remaining at atmospheric pressure.

20. The probe assembly of claim 19, wherein said sensor is a temperature sensor, and said closed end cap has fins emanating exteriorly therefrom to facilitate thermal transfer from said pressurized fluid process to said well.

* * * * *